US010322095B2

(12) United States Patent
Khan et al.

(10) Patent No.: US 10,322,095 B2
(45) Date of Patent: Jun. 18, 2019

(54) ENDOXIFEN FOR LOCAL TRANSDERMAL THERAPY TO THE BREAST

(71) Applicant: Northwestern University, Evanston, IL (US)

(72) Inventors: Seema Ahsan Khan, Chicago, IL (US); Oukseub Lee, Morton Grove, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/842,523

(22) Filed: Dec. 14, 2017

(65) Prior Publication Data
US 2018/0104196 A1    Apr. 19, 2018

Related U.S. Application Data

(63) Continuation of application No. 15/492,641, filed on Apr. 20, 2017, now abandoned.

(60) Provisional application No. 62/325,205, filed on Apr. 20, 2016.

(51) Int. Cl.
| A61K 31/35 | (2006.01) |
| A61K 31/138 | (2006.01) |
| A61K 9/00 | (2006.01) |
| A61K 47/12 | (2006.01) |
| A61K 47/10 | (2017.01) |
| A61K 9/06 | (2006.01) |

(52) U.S. Cl.
CPC .......... *A61K 31/138* (2013.01); *A61K 9/0014* (2013.01); *A61K 9/06* (2013.01); *A61K 47/10* (2013.01); *A61K 47/12* (2013.01)

(58) Field of Classification Search
CPC ..................................... A61K 31/35
USPC ....................................... 514/651
See application file for complete search history.

(56) References Cited

U.S. PATENT DOCUMENTS

| 2010/0112041 A1* | 5/2010 | Ahmad ............... A61K 9/0014 424/450 |
| 2012/0010245 A1 | 1/2012 | Masini-Eteve |
| 2012/0164075 A1 | 6/2012 | Ahmad |

OTHER PUBLICATIONS

Ackerman AB, Kessler G, Gyorfi T, Tsou HC, Gottlieb GJ (2007) Contrary view: the breast is not an organ per se, but a distinctive region of skin and subcutaneous tissue. Am J Dermatopathol 29(2):211-218.
Ahmad A, Shahabuddin S, Sheikh S, Kale P, Krishnappa M, Rane RC, Ahmad I (2010) Endoxifen, a new cornerstone of breast cancer therapy: demonstration of safety, tolerability, and systemic bioavailability in healthy human subjects. Clin Pharmacol Ther 88(6):814-817.
Bartek MJ, LaBudde JA, Maibach HI (1972) Skin permeability in vivo: comparison in rat, rabbit, pig and man. J Invest Dermatol 58(3):114-123.
Cuzick J, Otto F, Baron JA, Brown PH, Bum J, Greenwald P, Jankowski J, La VC, Meyskens F, Senn HJ et al (2009) Aspirin and non-steroidal anti-inflammatory drugs for cancer prevention: an international consensus statement. Lancet Oncol 10(5):501-507.
Cuzick J, Sestak I, Bonanni B, Costantino JP, Cummings S, Decensi A, Dowsett M, Forbes JF, Ford L, LaCroix AZ et al (2013) Selective oestrogen receptor modulators in prevention of breast cancer: an updated meta-analysis of individual participant data. Lancet 381(9880):1827-1834.
Cuzick J, Sestak I, Forbes JF, Dowsett M, Knox J, Cawthorn S, Saunders C, Roche N, Mansel RE, von MG et al (2013) Anastrozole for prevention of breast cancer in high-risk postmenopausal women (IBIS-II): an international, double-blind, randomized placebo-controlled trial. Lancet 383(9922):1040.
Day R, Ganz PA, Costantino JP, Cronin WM, Wickerham DL, Fisher B (1999) Health-related quality of life and tamoxifen in breast cancer prevention: a report from the National Surgical Adjuvant Breast and Bowel Project P-1 Study. J Clin Oncol 17(9):2659-2669.
Decensi A, Robertson C, Viale G, Pigatto F, Johansson H, Kisanga ER, Veronesi P, Torrisi R, Cazzaniga M, Mora S et al (2003) A randomized trial of low-dose tamoxifen on breast cancer proliferation and blood estrogenic biomarkers. J Natl Cancer Inst 95(11):779-790.
Dehghanyar P, Mayer BX, Namiranian K, Mascher H, Muller M, Brunner M (2004) Topical skin penetration of diclofenac after single- and multiple-dose application. Int J Clin Pharmacol Ther 42(7):353-359.
Fisher B, Costantino JP, Wickerham DL, Redmond CK, Kavanah M, Cronin WM, Vogel V, Robidoux A, Dimitrov N, Atkins J et al (1998) Tamoxifen for prevention of breast cancer: report of the National Surgical Adjuvant Breast and Bowel Project P-1 Study. J Natl Cancer Inst 90(18):1371-1388.
Goetz MP, Suman VA, Reid JR, Northfelt DW, Mahr MA, Dockter T, Haluska PJ, Kuffel M, Burhow S, Safgren S et al (2013) A first-in-human phase I study of the tamoxifen (TAM) metabolite, Z-endoxifen hydrochloride (Z-Endx) in women with aromatase inhibitor (AI) refractory metastatic breast cancer (MBC) (NCT01327781). The 2013 San Antonio Breast Cancer Symposium 2013.
Goss PE, Ingle JN, Ales-Martinez JE, Cheung AM, Chlebowski RT, Wactawski-Wende J, McTiernan A, Robbins J, Johnson KC, Martin LW et al (2011) Exemestane for breast-cancer prevention in postmenopausal women. N Engl J Med 364(25):2381-2391.

(Continued)

*Primary Examiner* — Raymond J Henley, III
(74) *Attorney, Agent, or Firm* — Quarles & Brady LLP

(57) ABSTRACT

Disclosed are methods and topical formulations for treating and/or preventing cell proliferative diseases and disorders including breast cancer and ductal carcinoma is situ (DCIS) using local transdermal therapy (LTT). The disclosed methods typically include administering topically to the breast or breasts of the patient a topical formulation comprising an effective dose of the tamoxifen metabolite, N-desmethyl-4-hydroxytamoxifen (i.e., endoxifen or ENX) for treating breast cancer. The topical formulation may be described as a transdermal formulation and the topical formulation may comprise, consist essentially of, or consist of endoxifen as an active ingredient.

20 Claims, 6 Drawing Sheets

(56) References Cited

OTHER PUBLICATIONS

Klimberg VS, Rubio IT, Henry R, Cowan C, Colvert M, Korourian S (1999) Subareolar versus peritumoral injection for location of the sentinel lymph node. Ann Surg 229(6):860-864.

Lee O, Ivancic D, Chatterton RT, Rademaker A, Khan SA (2011) In vitro human skin permeation of endoxifen: potential for local transdermal therapy for primary prevention and carcinoma in situ of the breast. Breast Cancer Targets Ther 3(1):61-70.

Lee O, Page K, Ivancic D, Helenowski I, Parini V, Sullivan ME, Margenthaler JA, Chatterton RT Jr, Jovanovic B, Dunn BK et al (2014) A randomized phase II presurgical trial of transdermal 4-hydroxytamoxifen gel versus oral tamoxifen in women with ductal carcinoma in situ of the breast. Clin Cancer Res 20(14):3672-3682.

Lim YC, Desta Z, Flockhart DA, Skaar TC (2005) Endoxifen (4-hydroxy-N-desmethyl-tamoxifen) has anti-estrogenic affects in breast cancer cells with potency similar to 4-hydroxy-tamoxifen. Cancer Chemother Pharmacol 55(5):471-478.

Lim YC, Li L, Desta Z, Zhao Q, Rae JM, Flockhart DA, Skaar TC (2006) Endoxifen, a secondary metabolite of tamoxifen, and 4-OH-tamoxifen induce similar changes in global gene expression patterns in MCF-7 breast cancer cells. J Pharmacol Exp Ther 318(2):503-512.

Mansel R, Goyal A, Nestour EL, Masini-Eteve V, O'Connell K (2007) A phase II trial of Afimoxifene (4-hydroxytamoxifen gel) for cyclical mastalgia in premenopausal women. Breast Cancer Res Treat 106(3):389-397.

McCarberg BH, Argoff CE (2010) Topical diclofenac epolamine patch 1.3% for treatment of acute pain caused by soft tissue injury. Int J Clin Pract 64(11):1546-1553.

Morimoto Y, Hatanaka T, Sugibayashi K, Omiya H (1992) Prediction of skin permeability of drugs: comparison of human and hairless rat skin. J Pharm Pharmacol 44(8):634-639.

Port ER, Montgomery LL, Heerdt AS, Borgen PI (2001) Patient reluctance toward tamoxifen use for breast cancer primary prevention. Ann Surg Oncol 8(7):580-585.

Povoski SP, Olsen JO, Young DC, Clarke J, Burak WE, Walker MJ, Carson WE, Yee LD, Agnese DM, Farrar WB (2006) Prospective Randomized trial comparing intradermal, intraparenchymal, and subareolar injection routes for sentinel lymph node mapping and biopsy in breast cancer. Ann Surg Oncol 13(2):10-11.

Pujol H, Girault J, Rouanet P, Fournier S, Grenier J, Simony J, Fourtillan JB, Pujol JL (1995) Phase I study of percutaneous 4-hydroxy-tamoxifen with analyses of 4-hydroxy-tamoxifen concentrations in breast cancer and normal breast tissue. Cancer Chemother Pharmacol 36(6):493-498.

Robinson SP, Langan-Fahey SM, Johnson DA, Jordan VC (1991) Metabolites, pharmacodynamics, and pharmacokinetics of tamoxifen in rats and mice compared to the breast cancer patient. Drug Metab Dispos 19(1):36-43.

Rouanet P, Linares-Cruz G, Dravet F, Poujol S, Gourgou S, Simony-Lafontaine J, Grenier J, Kramar A, Girault J, Le Nestour E et al (2005) Neoadjuvant percutaneous 4-hydroxytamoxifen decreases breast tumoral cell proliferation: a prospective controlled randomized study comparing three doses of 4-hydroxytamoxifen gel to oral tamoxifen. J Clin Oncol 23(13):2980-2987.

Suami H, Pan WR, Mann GB, Taylor GI (2008) The lymphatic anatomy of the breast and its implications for sentinel lymph node biopsy: a human cadaver study. Ann Surg Oncol 15(3):863-871.

Stearns V, Mori T, Jacobs LK, Khouri NF, Gabrielson E, Yoshida T, Kominsky SL, Huso DL, Jeter S, Powers P et al (2011) Preclinical and clinical evaluation of intraductally administered agents in early breast cancer. Sci Transl Med 3(106):106ra108.

Wiehle R, Lantvit D, Yamada T, Christov K (2011) CDB-4124, a progesterone receptor modulator, inhibits mammary carcinogenesis by suppressing cell proliferation and inducing apoptosis. Cancer Prev Res (Phila) 4(3):414-424.

Wiehle RD, Christov K, Mehta R (2007) Anti-progestins suppress the growth of established tumors induced by 7,12-dimethylbenz(a) anthracene: comparison between RU486 and a new 21-substituted-19-nor-progestin. Oncol Rep 18(1):167-174.

Yang Y, Pearson RM, Lee O, Lee CW, Chatterton RT, Khan SA, Hong S (2014) Dendron-based micelles for topical delivery of endoxifen: a potential chemo-preventive medicine for breast cancer. Adv Funct Mater 24(17):2442-2449.

\* cited by examiner

ENDOXIFEN FOR LOCAL TRANSDERMAL THERAPY TO THE BREAST

CROSS-REFERENCED TO RELATED PATENT APPLICATIONS

The present application is a continuation application of U.S. application Ser. No. 15/492,641, filed on Apr. 20, 2017, which application claims the benefit of priority to U.S. Provisional Application No. 62/325,205, filed on Apr. 20, 2016, the contents of which are incorporated herein by reference in their entireties.

BACKGROUND

The field of the invention relates to methods for treating and/or preventing cell proliferation diseases and disorders such as cancer. In particular, the field of the invention relates to methods for treating and/or preventing breast cancer and/or ductal carcinoma in situ (DCIS) that include administering a topical formulation of the tamoxifen metabolite N-desmethyl-4-hydroxytamoxifen, otherwise called endoxifen.

Despite large Phase III clinical trials that have established the success of selective estrogen receptor modulators (SERMs) for breast cancer prevention and therapy of duct carcinoma in situ (DCIS), uptake of SERMS by women with these problems has been poor. (Lee et. al., Local transdermal therapy to the breast for breast cancer prevention and DCIS therapy: preclinical and clinical evaluation. *Cancer Chemother Pharmacol.* 2015. November; Epub ahead of print. PMID: 26560487 and Lee et. al., Novel routes for administering chemoprevention: Local transdermal therapy to the breasts. *Semin Onc.* 2016 February; 43(1):107-15. PMID: 26970129). Reasons include quality of life impairments, the possibility of serious side effects, and reluctance by healthy women to take oral medication for prevention. However, breast cancer prevention requires only that the breast be exposed to the drug; systemic exposure is both unnecessary and harmful. For example, 5 years of systemic exposure with oral TAM leads to benefits to the breast and bone, but with costs to quality of life, and health. An alternative to oral delivery is that of transdermal delivery of drugs through the breast skin; its advantages include low systemic exposure, the avoidance of fast hepatic metabolism, and simplicity of application which will allow dissemination across the globe. Therefore, local transdermal therapy (LTT) to the breast is likely to improve the tolerability and the acceptance of pharmacological cancer prevention regimens by women. Consequently, we have introduced the concept of transdermal delivery of SERMs for breast cancer prevention and DCIS therapy (see Lee et al. A randomized phase II presurgical trial of transdermal 4-Hydroxytamoxifen gel versus oral tamoxifen in women with ductal carcinoma in situ of the breast. *Clinical Cancer Res,* 2014 Jul. 15; 20(14):3672-82. doi: 10.1158/1078-0432.CCR-13-3045 and Lee et. al., Local transdermal therapy to the breast for breast cancer prevention and DCIS therapy: preclinical and clinical evaluation. *Cancer Chemother Pharmacol.* 2015. November; Epub ahead of print. PMID: 26560487 and Lee et. al., Novel routes for administering chemoprevention: Local transdermal therapy to the breasts. *Semin Onc.* 2016 February; 43(1):107-15. PMID: 26970129).

SUMMARY

Disclosed are methods for treating and/or preventing cell proliferative diseases and disorders in patient in need thereof. Cell proliferative diseases and disorders treated and/or prevented by the disclosed methods may include breast cancer and ductal cancer in situ (DCIS). The disclosed methods typically include administering topically to the breast or breasts of the patient a topical formulation comprising an effective dose of the tamoxifen metabolite, N-desmethyl-4-hydroxytamoxifen (i.e., endoxifen or ENX) for treating breast cancer. The topical formulation may be described as a transdermal formulation and the topical formulation may comprise, consist essentially of, or consist of endoxifen as an active ingredient. The topical formulation of the disclosed methods may include a carrier, excipient, or diluent.

The topical formulation may include one or more chemical permeation enhancers (CPEs) for transdermal drug delivery. In some embodiments, the topical formulation includes a fatty acid. Suitable fatty acids may include, but are not limited to oleic acid. The topical formulation of the disclosed methods may include an alcohol. Suitable alcohols may include, but are not limited to ethanol and/or isopropyl alcohol. The topical formulation of the disclosed methods may include a gel, which optionally may be administered via a patch. The gel may include a gelling polymer as known in the art. Suitable gelling polymers may include, but are not limited to cellulose derivatives and carbomer polymers.

The topical formulation typically comprises endoxifen at an effective dose for treating and/or preventing breast concentration, and in the disclosed methods, endoxifen preferably is administered to the patient at an effective dose for treating and/or preventing breast cancer. In the disclosed methods, preferably a higher dose of endoxifen is delivered to the breast or breasts of the patient relative to the dose delivered to the plasma of the patient.

The disclosed methods and topical composition may be utilized for treating and/or preventing breast cancer. In some embodiments, the disclosed methods and topical compositions may be utilized in pre-operative therapy and/or post-operative therapy for a patient having ductal carcinoma in situ of the breast. In other embodiments, the disclosed methods and topical formulation may be utilized in therapy to alleviate breast pain. In even further embodiments, the disclosed methods and topical formulation may be utilized to reduce breast density, for example, prior to breast imaging in order to improve imaging of the breast.

DETAILED DESCRIPTION

Figure 1:
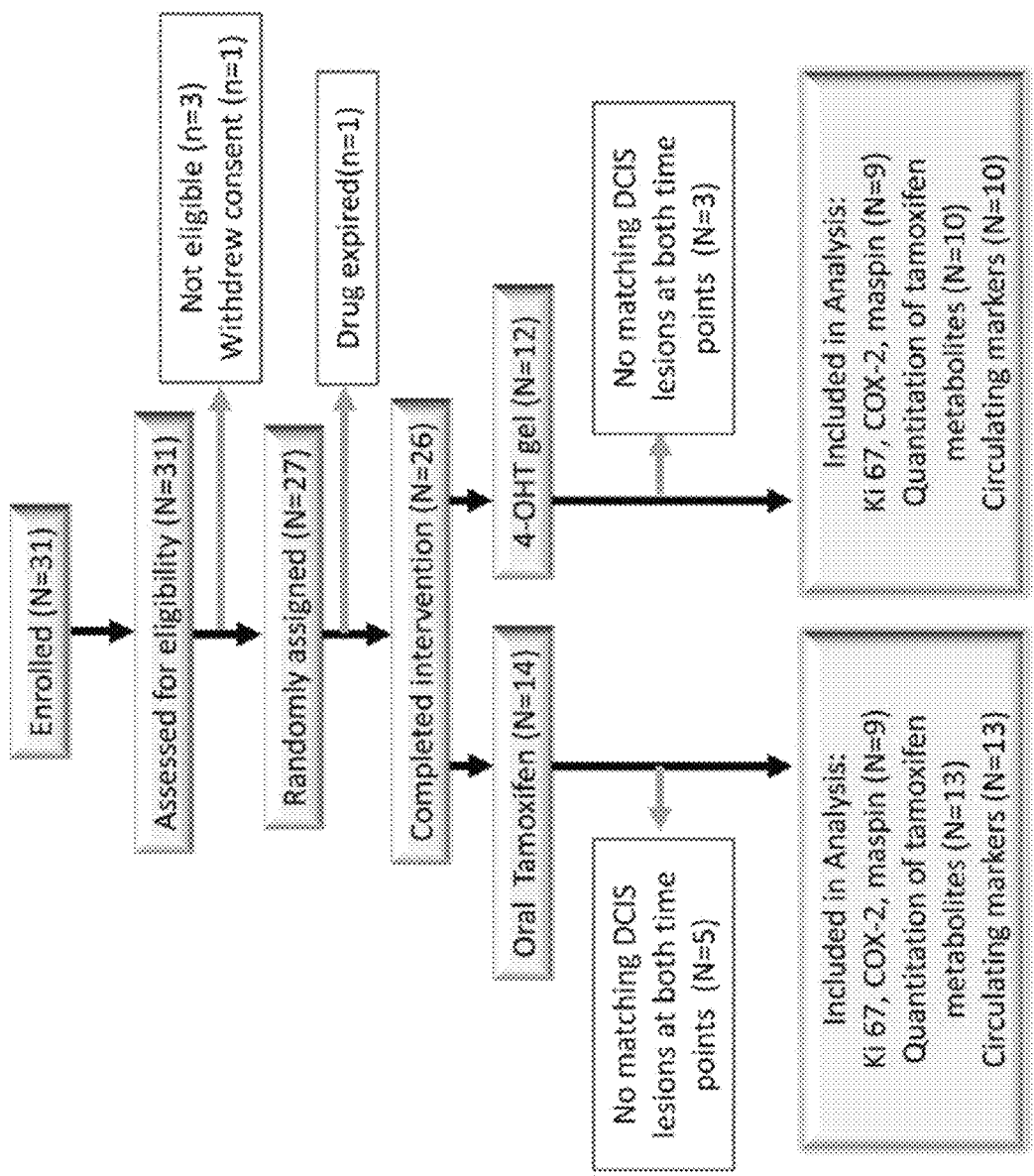
FIG. 1. CONSORT diagram (participate flow chart).

The present invention is described herein using several definitions, as set forth below and throughout the application.

Unless otherwise specified or indicated by context, the terms "a", "an", and "the" mean "one or more." For example, "a compound" should be interpreted to mean "one or more compounds."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "patient" may be interchangeable with "subject" or "individual" and means an animal, which may be a human or non-human animal, in need of treatment.

A "patient in need thereof" may include a patient having a disease, disorder, or condition that is responsive to therapy with tamoxifen and/or metabolites thereof such as N-desmethyl-4-hydroxytamoxifen (i.e., endoxifen or ENX) or 4-hydroxytamoxifen (i.e., 4-OHT). In particular, a "patient in need thereof" may include a patient having a disease, disorder, or condition that is responsive to therapy that includes administering a topical formulation comprising endoxifen, where the therapy delivers an effective dose of tamoxifen and/or metabolites thereof at the underlying tissue at the site of topical administration and preferably delivers only a minimal dose systemically, for example, as measured in the patient's plasma. As such, a "patient in need thereof" may include a patient having a disease or disorder that is responsive to local transdermal therapy (LTT) with endoxifen. For example, a "patient in need thereof" may include a patient having a cell proliferative disease, disorder, or condition such as cancer, including breast cancer and ductal carcinoma in situ (DCIS).

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

The topical formulation may include one or more chemical permeation enhancers (CPEs) for transdermal drug delivery. CPEs are known in the art. (See, e.g., Williams et al., "Penetration enhancers," Adv. Drug Deliv. Rev. 2004 Mar. 27; 56(5):603-18; and Pathan et al., "Chemical Penetration Enhancers for Transdermal Drug Delivery System," Trop. J. Pharma. Res., April 2009; 8(2): 173-179, the contents of which are incorporated herein by reference in their entireties). Suitable CPEs may include, but are not limited to solvents (e.g., monohydric alcohols such as methanol, ethanol, propanol, isopropanol), fatty acids (e.g., oleic acid, caprylic acid), surfactants (e.g., ionic or non-ionic detergents), bile salts and derivatives, micelles/liposomes or micelle-forming or liposome-forming components (e.g., phospholipids), sulfoxides, terpenes and terpenoids, polyols, urea and derivatives, and chelating agents. A non-limiting list of CPEs may include methanol, ethanol, propylene glycol, diethylene glycol monoethyl ether (transcutol), oleic acid, caprylic acid, menthol, nerol, camphor, methyl salicylate, Tween 80, SDS, benzalkonium chloride, polyoxyl 40 hydrogenated castor oil, didecyldimethylammonium bromide (DDAB), didecyltrimethylammonium bromide (DTAB), polysorbates, Na glyacolate, Na deoxycholate, EDTA, citric acid, DMSO, DMF, propylene glycol, polyethylene glycol, glycerol, urea, terpenes and terpenoids, phospholipids, water, and mixtures thereof.

In some embodiments, the topical formulation includes a fatty acid. Suitable fatty acids may include, but are not limited to oleic acid. The topical formulation of the disclosed methods may include an alcohol. Suitable alcohols may include, but are not limited to ethanol and/or isopropyl alcohol. The topical formulation of the disclosed methods may include a gel, which optionally may be administered via a patch. The gel may include a gelling polymer as known in the art. Suitable gelling polymers may include, but are not limited to cellulose derivatives and carbomer polymers.

ILLUSTRATIVE EMBODIMENTS

Disclosed are methods for treating and/or preventing cell proliferative diseases and disorders in patient in need thereof. Cell proliferative diseases and disorders treated and/or prevented by the disclosed methods may include breast cancer and ductal cancer in situ (DCIS). The disclosed methods typically include administering topically to the breast or breasts of the patient a topical formulation comprising an effective dose of the tamoxifen metabolite, N-desmethyl-4-hydroxytamoxifen (i.e., endoxifen or ENX) for treating breast cancer. In some embodiments, the topical formulation comprises, consists essentially of, or consists of endoxifen as an active ingredient. The topical formulation may be described as a transdermal formulation.

The topical formulation of the disclosed methods may include a carrier, excipient, or diluent. In some embodiments, the topical formulation includes one or more chemical penetration enhancers (CPEs) as known in the art and as described herein. The one or more CPEs may be present in the topical formulation at any suitable concentration. Suitable concentrations for the one or more CPEs in the topical formulation may include but are not limited to concentrations of at least about, or no more than about, 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80% (w/w), or concentrations within a range bounded by any two of these values (e.g., 0.1-2% (w/w)).

In some embodiments, the topical formulation includes a fatty acid. Suitable fatty acids may include, but are not limited to saturated or unsaturated fatty acids having 12-28 carbon atoms (or preferably 14-20). The topical formulation may include the fatty acid at any suitable concentration, for example, at a concentration of at least about, or at a concentration of no more than about, any of the following values: 0.01%, 0.05%, 0.1%, 0.5%, 1.0%, 2.0%, 3.0%, 4.0%, 5.0%, 6.0%, 7.0%, 8.0%, 9.0%, or 10.0% (w/w), or at a concentration within a range bounded by any two of these values. The fatty acid may be a monounsaturated fatty acid or a polyunsaturated fatty acid. In some embodiments, the fatty acid is liquid at room temperature and/or has a melting temperature of less than about 20° C. Preferably, the fatty acid is oleic acid.

The topical formulation of the disclosed methods may include alcohol (e.g., ethanol and/or isopropyl alcohol). In some embodiments, the topical formulation comprises alcohol at a concentration of at least about, or at a concentration of no more than about, any of the following values 1%, 2%, 3%, 4%, 5%, 10%, 20%, 30%, 40%, 50%, 60%, 70%, 80% (w/w), or at a concentration within a range bounded by any two of these values.

The topical formulation of the disclosed methods may include a gel, which optionally may be administered via a patch. The gel may include a gelling polymer as known in the art, including cellulose derivatives (e.g., hydroxyethyl cellulose, methylcellulose, hydroxypropyl methyl cellulose, hydroxypropyl cellulose, carboxymethyl cellulose, and carbomer polymers such as poloxamer, polyvinyl alcohol, polyacrylamide, polyethylene and its co-polymers). (See e.g., Kaur et al., Asian J. Biomedia & Pharma Sci., 15 Mar. 2013, e-ISSN: 2249-622x, the content of which is incorporated herein by reference in its entirety). Preferably, the gelling polymer is present in the topical formulation at a concentration of at least about, or at a concentration of no more than about, any of the following values: 0.1%, 0.5%, 1.0%, 1.5%, 2.0%, 3.0%, 4.0%, 5.0% (w/w), or within a concentration within a range bounded by any two of these values.

The topical formulation typically comprises endoxifen at an effective dose for treating and/or preventing breast concentration. In some embodiments, the endoxifen is present in the topical formulation at a concentration of at least about, or at a concentration of no more than about, any of the following values: 0.01 mg/ml, 0.05 mg/ml, 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, or at a concentration within a range bounded by any two of these values.

In the disclosed methods, endoxifen preferably is administered to the patient at an effective dose for treating and/or preventing breast cancer. In some embodiments of the disclosed methods, the endoxifen is administered at a dose per bodyweight of the patient (mg/kg) per day of at least about, or at a dose of no more than about, any of the following values: 0.1 mg/kg/day, 0.5 mg/kg/day, 1.0 mg/kg/day, 2.0 mg/kg/day, 3.0 mg/kg/day, 4.0 mg/kg/day, 5.0 mg/kg/day, 6.0 mg/kg/day, 7.0 mg/kg/day, 8.0 mg/kg/day, 9.0 mg/kg/day, 10 mg/kg/day.

In the disclosed methods, preferably a higher dose of endoxifen is delivered to the breast or breasts of the patient relative to the dose delivered to the plasma of the patient. In some embodiments of the disclosed methods, the dose delivered to the breast of the patient (ng/g breast tissue) is at least about, or no more than about, any of the following values: 0.1 ng/g, 0.5 ng/g, 1.0 ng/g, 2.0 ng/g, 3.0 ng/g, 4.0 ng/g, 5.0 ng/g, 6.0 ng/g, 7.0 ng/g, 8.0 ng/g, 9.0 ng/g, 10 ng/g, 15 ng/g, 20 ng/g, 25 ng/g, or 30 ng/g, or at a dose within a range bounded by any of these values. In further embodiments of the disclosed methods, the dose delivered to the plasma of the patient is no more than about, or at least about, any of the following values: 20 ng/ml, 15 ng/ml, 10 ng/ml, 5 ng/ml, 4 ng/ml, 3 ng/ml, 2 ng/ml, 1 ng/ml, 0.5 ng/ml, 0.1 ng/ml, or at a dose within a range bounded by any of these values. Preferably in the disclosed methods, the ratio (R) of the dose of endoxifen thereof delivered to the breast of the patient ($D_{Breast}$ in ng/g) to the dose delivered to the plasma of the patient ($D_{Plasma}$ in ng/ml) is greater than about any of the following values: 0.1, 0.5, 1, 2, 3, 4, 5, 10, 20, 30, 40, 50, or at a ratio within a range bounded by any of these values (assuming that 1 g tissue is approximately equal in mass to 1 ml of plasma).

Also disclosed are topical formulations as utilized in the disclosed methods. As such, the disclosed formulations typical include an effective dose of endoxifen for treating breast cancer. Typically, the topical formulation include a carrier, excipient, or diluent, which may include, but are not limited to, a fatty acid, an alcohol, and/or a gelling polymer.

The disclosed methods and topical composition may be utilized for treating and/or preventing breast cancer. In some embodiments, the disclosed methods and topical compositions may be utilized in post-operative therapy for a patient having ductal carcinoma in situ of the breast. In other embodiments, the disclosed methods and topical formulation may be utilized in therapy to alleviate breast pain. In even further embodiments, the disclosed methods and topical formulation may be utilized to reduce breast density, for example, prior to breast imaging in order to improve imaging of the breast.

The disclosed methods and topical formulations utilize and/or include taxomifen and/or metabolites thereof for local transdermal therapy (LTT). Endoxifen is particularly well suited for development as a breast LTT agent and has a structure:

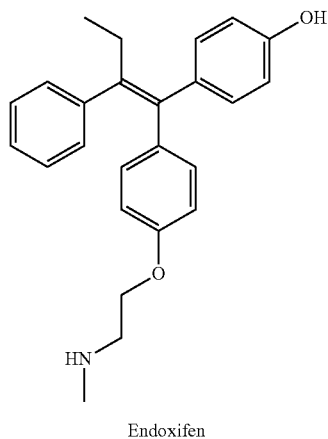 [SMILES: CC/C(=C(\c1ccc(O)cc1)c1ccc(OCCNC)cc1)c1ccccc1]

Endoxifen

Like 4-OHT, the binding affinities of ENX are 25-fold greater for ERα and 56-fold greater for ERβ than that of TAM. (See Lim et al. Endoxifen (4-hydroxy-N-desmethyl-tamoxifen) has antiestrogenic effects in breast cancer cells with potency similar to 4-hydroxy-tamoxifen. *Cancer Chemother Pharmacol* 2005, 55: 471-478; and Lim et al.: Endoxifen, a secondary metabolite of tamoxifen, and 4-OH-tamoxifen induce similar changes in global gene expression patterns in MCF-7 breast cancer cells. *J Pharmacol Exp Ther* 2006, 318: 503-512). ENX is expected to be more efficacious than 4-OHT related to its proteosomic degradation of ERα, and the possibility of more selective anti-estrogenic effects. (See Goetz et al.: Pharmacogenetics of tamoxifen biotransformation is associated with clinical outcomes of efficacy and hot flashes. *J Clin Oncol* 2005, 23: 9312-9318; Goetz et al.: The impact of cytochrome P450 2D6 metabolism in women receiving adjuvant tamoxifen. *Breast Cancer Res Treat* 2007, 101: 113-121; and Wu et al.: The tamoxifen metabolite, endoxifen, is a potent antiestrogen that targets estrogen receptor alpha for degradation in breast cancer cells. *Cancer Res* 2009, 69: 1722-1727). Its specific toxicity profile is under study, but results from the Mayo group suggest that, in terms of uterine weight, luminal epithelial cell height, and cell proliferation in the stroma and luminal epithelium of the uterus, ENX has similar uterotrophic effects to TAM when administered orally to rats. (See Schweikart et al.: Comparative Uterotrophic Effects of Endoxifen and Tamoxifen in Ovariectomized Sprague-Dawley Rats. *Toxicol Pathol* 2014). If it shares the toxicity of the parent drug and its dermal permeation is equivalent to that of 4-OHT (or better), ENX is an excellent candidate for LTT. Additionally, the chemical structure of ENX would render it more suitable for transdermal delivery. It is smaller and more polar than 4-OHT; one methyl group at a tertiary amine is replaced with a hydrogen, resulting in a secondary amine, which is more hydrophilic than the tertiary amine of 4-OHT. With the addition of a permeation enhancer such as oleic acid (OA) which makes the stratum corneum fluidic (see Fang et al.: Effect of enhancers and retarders on percutaneous absorption of flurbiprofen from hydrogels. *Int J Pharm* 2003, 250: 313-325; and Yu et al.: In vitro visualization and quantification of oleic acid induced changes in transdermal transport using two-photon fluorescence microscopy. *J Invest Dermatol* 2001, 117: 16-25), and ethanol, which gives a continuous driving force (see Ogiso et al.: Percutaneous penetration of fluorescein isothiocyanate-dextrans and the mechanism for enhancement effect of enhancers on the intercellular penetration. *Biol Pharm Bull* 1995, 18: 1566-1571; and Williams et al.: Penetration enhancers. *Adv Drug Deliv Rev* 2004, 56: 603-618). ENX moves faster through the skin than 4-OHT. The amine group of ENX may provide a favorable balance of hydrophilic and hydrophobic properties, making ENX traverse the stratum corneum more easily. One suitable transdermal formulation of endoxifen includes endoxifen free base in a 60% alcoholic gel, with 0.5% oleic acid, and a gelling polymer such as Klucel™ hydroxypropylcellulose. Novel routs for administering chemoprevention are disclosed in Lee et al., Semin Oncol. 2016 February; 43(1):107-15, the content of which is incorporated herein by reference in its entirety.

The disclosed topical formulations may include tamoxifen or a metabolite thereof such as endoxifen (ENX) or 4-OHT, as a free base, a free acid (which is optionally hydrated) or a pharmaceutically acceptable salt thereof. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

There are currently no approved transdermal formulations of medication for breast cancer prevention or therapy of carcinoma in situ. Additionally, about 40% of women have dense breasts and mammography often misses cancer in this group. The transdermal delivery of tamoxifen metabolites such as endoxifen will enable these women to use a drug applied to the breast skin that should have good efficacy in reducing mammographic density.

ILLUSTRATIVE EMBODIMENTS

The following embodiments are illustrative and should be interpreted to limit the scope of the claimed subject matter.

Embodiment 1

A method for treating and/or preventing breast cancer and ductal cancer in situ (DCIS) in a patient in need thereof, the method comprising administering topically to the breast or breasts of the patient a topical formulation comprising an effective dose of endoxifen for treating breast cancer.

Embodiment 2

The method of embodiment 1, wherein the topical formulation is a transdermal formulation comprising one or more chemical penetration enhancers (CPEs).

Embodiment 3

The method of embodiment 1 or 2, wherein the topical formulation comprises at least about 0.1% of a saturated or unsaturated fatty acid having 12-28 carbon atoms.

Embodiment 4

The method of embodiment 3, wherein the topical formulation comprises a fatty acid at a concentration of at least about, or at a concentration of no more than about, any of the following values: 0.01%, 0.05%, 0.1%, 0.5%, 1.0%, 2.0%, 3.0%, 4.0%, 5.0%, 6.0%, 7.0%, 8.0%, 9.0%, or 10.0% (w/w), or at a concentration within a range bounded by any two of these values.

Embodiment 5

The method of embodiment 3 or 4, wherein the fatty acid is a monounsaturated fatty acid or a polyunsaturated fatty acid.

Embodiment 6

The method of any of claims 3-5, wherein the fatty acid has a melting temperature of less than about 20° C.

Embodiment 7

The method of any of claims 3-6, wherein the fatty acid has 14-20 carbon atoms.

Embodiment 8

The method of any of claims 3-7, wherein the fatty acid is oleic acid.

Embodiment 9

The method of any of the foregoing claims, wherein the topical formulation comprises alcohol, preferably at a concentration of at least about, or at a concentration of no more than about, any of the following values 1%, 2%, 3%, 4%, 5%, 10%, 20%, 30%, 40%, 50%, 60%, 70%, 80% (w/w), or at a concentration within a range bounded by any two of these values.

Embodiment 10

The method of any of the foregoing claims, wherein the topical formulation is a gel comprising a gelling polymer, preferably at a concentration of at least about, or at a concentration of no more than about, any of the following values: 0.1%, 0.5%, 1.0%, 1.5%, 2.0%, 3.0%, 4.0%, 5.0% (w/w), or within a concentration within a range bounded by any two of these values.

Embodiment 11

The method of any of the foregoing claims, wherein the endoxifen is present in the topical formulation at a concentration of at least about, or at a concentration of no more than about, any of the following values: 0.01 mg/ml, 0.05 mg/ml, 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 25 mg/ml, 30 mg/ml or at a concentration within a range bounded by any two of these values.

Embodiment 12

The method of any of the foregoing claims, wherein the endoxifen is administered at a dose per bodyweight of the patient (mg/kg) per day of at least about, or at a concentration of no more than about, any of the following values: 0.01 mg/kg/day, 0.05 mg/kg/day, 0.1 mg/kg/day, 0.5 mg/kg/day, 1.0 mg/kg/day, 2.0 mg/kg/day, 3.0 mg/kg/day, 4.0 mg/kg/ day, 5.0 mg/kg/day, 6.0 mg/kg/day, 7.0 mg/kg/day, 8.0 mg/kg/day, 9.0 mg/kg/day, 10 mg/kg/day, 15 mg/kg/day, 20 mg/kg/day, 25 mg/kg/day, 30 mg/kg/day or at a dose within a range bounded by any two of these values.

Embodiment 13

The method of any of the foregoing claims, wherein the dose delivered to the breast of the patient (ng/g breast tissue) is at least about, or no more than about, any of the following values: 0.01 ng/g, 0.05 ng/g, 0.1 ng/g, 0.5 ng/g, 1.0 ng/g, 2.0 ng/g, 3.0 ng/g, 4.0 ng/g, 5.0 ng/g, 6.0 ng/g, 7.0 ng/g, 8.0 ng/g, 9.0 ng/g, 10 ng/g, 15 ng/g, 20 ng/g, 25 ng/g, 30 ng/g, or at a dose within a range bounded by any of these values.

Embodiment 14

The method of any of the foregoing claims, wherein the dose delivered to the plasma of the patient is no more than about, or at least about, any of the following values: 30 ng/ml, 25 ng/ml, 20 ng/ml, 15 ng/ml, 10 ng/ml, 5 ng/ml, 4 ng/ml, 3 ng/ml, 2 ng/ml, 1 ng/ml, 0.5 ng/ml, 0.1 ng/ml, 0.05 ng/ml, 0.01 ng/ml, or at a dose within a range bounded by any of these values.

Embodiment 15

The method of any of the foregoing claims, wherein the ratio (R) of the dose of endoxifen delivered to the breast of the patient ($D_{Breast}$) to the dose delivered to the plasma of the patient ($D_{Plasma}$) is greater than about any of the following values: 0.1, 0.5, 1, 2, 3, 4, 5, 10, 20, 30, 40, 50, or at a ratio within a range bounded by any of these values.

Embodiment 16

A topical formulation for treating and/or preventing breast cancer and ductal cancer in situ (DCIS) in a patient in need thereof, the topical formulation comprising an effective dose of endoxifen for treating breast cancer.

Embodiment 17

The topical formulation of embodiment 16, wherein the topical formulation is a transdermal formulation.

Embodiment 18

The topical formulation of embodiment 16 or 17, wherein the topical formulation comprises at least about 0.1% (w/w) of a saturated or unsaturated fatty acid and the fatty acid has 12-28 carbon atoms.

Embodiment 19

The topical formulation of embodiment 18, wherein the topical formulation comprises a fatty acid at a concentration of at least about, or at a concentration of no more than about, any of the following values: 0.01%, 0.05%, 0.1% 0.5%, 1.0%, 2.0%, 3.0%, 4.0%, 5.0%, 6.0%, 7.0%, 8.0%, 9.0%, or 10.0% (w/w), or at a concentration within a range bounded by any two of these values.

Embodiment 20

The topical formulation of embodiment 18 or 19, wherein the fatty acid is a monounsaturated fatty acid or a polyunsaturated fatty acid.

Embodiment 21

The topical formulation of any of claims 18-20, wherein the fatty acid has a melting temperature of less than about 20° C.

Embodiment 22

The topical formulation of any of claims 18-21, wherein the fatty acid has 14-20 carbon atoms.

Embodiment 23

The topical formulation of any of claims 18-22, wherein the fatty acid is oleic acid.

Embodiment 24

The topical formulation of any of claims 16-23, wherein the topical formulation comprises alcohol, preferably at a concentration of at least about, or at a concentration of no more than about, any of the following values 1%, 2%, 3%, 4%, 5%, 10%, 20%, 30%, 40%, 50%, 60%, 70%, 80% (w/w), or at a concentration within a range bounded by any two of these values.

Embodiment 25

The topical formulation of any of claims 16-24, wherein the topical formulation is a gel comprising a gelling polymer, preferably at a concentration of at least about, or at a concentration of no more than about, any of the following values: 0.1%, 0.5%, 1.0%, 1.5%, 2.0%, 3.0%, 4.0%, 5.0% (w/w), or within a concentration within a range bounded by any two of these values.

Embodiment 26

The topical formulation of any of claims 16-25, wherein the endoxifen is present in the topical formulation at a concentration of at least about, or at a concentration of no more than about, any of the following values: 0.01 mg/ml, 0.05 mg/ml, 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, or at a concentration within a range bounded by any two of these values.

Embodiment 27

The topical formulation of any of claims 16-26, wherein the topical formulation is formulated to deliver endoxifen at a dose per bodyweight of the patient (mg/kg) per day of at least about, or at a concentration of no more than about, any of the following values: 0.01 mg/kg/day, 0.05 mg/kg/day, 0.1 mg/kg/day, 0.5 mg/kg/day, 1.0 mg/kg/day, 2.0 mg/kg/day, 3.0 mg/kg/day, 4.0 mg/kg/day, 5.0 mg/kg/day, 6.0 mg/kg/day, 7.0 mg/kg/day, 8.0 mg/kg/day, 9.0 mg/kg/day, 10 mg/kg/day, 15 mg/kg/day, 20 mg/kg/day, 25 mg/kg/day, 30 mg/kg/day or at a dose bounded by any two of these values.

Embodiment 28

The topical formulation of any of claims 16-27, wherein the topical formulation is formulated to deliver a dose of endoxifen to the breast of the patient (ng/g breast tissue) of at least about any of the following values: 0.01 ng/g, 0.05 ng/g, 0.1 ng/g, 0.5 ng/g, 1.0 ng/g, 2.0 ng/g, 3.0 ng/g, 4.0 ng/g, 5.0 ng/g, 6.0 ng/g, 7.0 ng/g, 8.0 ng/g, 9.0 ng/g, 10 ng/g, 15 ng/g, 20 ng/g, 25 ng/g, 30 ng/g, or at a dose within a range bounded by any of these values.

Embodiment 29

The topical formulation of any of claims 16-28, wherein the topical formulation is formulated to deliver a dose of endoxifen to the plasma of the patient that is no more than about any of the following values: 30 ng/ml, 25 ng/ml 20 ng/ml, 15 ng/ml, 10 ng/ml, 5 ng/ml, 1 ng/ml, 0.5 ng/ml, 0.1 ng/ml, 0.05 ng/ml, 0.01 ng/ml or at a dose within a range bounded by any of these values.

Embodiment 30

The topical formulation of any of claims 16-29, wherein the ratio (R) of the dose of endoxifen delivered to the breast of the patient ($D_{Breast}$) to the dose delivered to the plasma of the patient ($D_{Plasma}$) is greater than about any of the following values: 0.1, 0.5, 1, 2, 3, 4, 5, 10, 20, 30, 40, 50, or at a ratio within a range bounded by any of these values.

EXAMPLES

The following Examples are illustrative and are not intended to limit the scope of the claimed subject matter.

Example 1

Reference is made to Lee et al., "A randomized phase II presurgical trial of transdermal 4-Hydroxytamoxifen gel versus oral tamoxifen in women with ductal carcinoma in situ of the breast," Clin. Cancer Res. 2014 July 15; 20(14): 3672-3682, the content of which is incorporated by reference in the application in its entirety.

Abstract

Purpose.

Local transdermal therapy to the breast may achieve effective target-organ drug delivery, while diminishing systemic effects. We conducted a randomized, double-blind, placebocontrolled phase II trial comparing transdermal 4-hydroxytamoxifen gel (4-OHT) to oral tamoxifen (oral-T) in women with ductal carcinoma in-situ (DCIS).

Methods.

27pre and postmenopausal women were randomized to 4-OHT (4 mg/day) or oral-T (20 mg/day) for 6-10 weeks before surgery. Plasma, nipple aspirate fluid, and breast adipose tissue concentrations of tamoxifen and its major metabolites were determined by liquid chromatography tandem mass spectrometry. The primary endpoint was Ki67 labeling in DCIS lesions, measured by immunohistochemistry. In plasma, insulin-like growth factor-1 (IGF-1), sex hormone-binding globulin (SHBG), and coagulation protein concentrations were determined.

Results.

Post-therapy Ki-67 decreased by 3.4% in the 4-OHT and 5.1% in the oral-T group (p<0.03 in both, between-group p=0.99). Mean plasma 4-OHT was 0.2 and 1.1 ng/mL in 4-OHT and oral groups, respectively (p=0.0003), while mean breast adipose tissue concentrations of 4-OHT were 5.8 ng/g in the 4-OHT group and 5.4 ng/g in the oral group (p=0.88). There were significant increases in plasma SHBG, Factor VIII and von Willebrand factor and a significant decrease in plasma IGF-1 with oral-T, but not with 4-OHT. The incidence of hot flashes was similar in both groups.

Conclusions.

The anti-proliferative effect of 4-OHT gel applied to breast skin was similar to that of oral-T, but effects on endocrine and coagulation parameters were reduced. These findings support the further evaluation of local transdermal therapy for DCIS and breast cancer prevention.

Introduction

Mammary ductal carcinoma in-situ (DCIS) accounts for 20% of new breast cancers [1], with 57,000 new cases diagnosed in the US in 2011 [2]. Although disease-specific survival rates approach 98% [3], the risk for the development of subsequent invasive breast cancer may reach 30% following local therapy [4], so that DCIS patients are advised to undertake systemic therapy in the form of oral tamoxifen (oral-T) in order to further reduce the risk of new (local) breast events.

Despite the success of tamoxifen in reducing recurrence risk of estrogen receptor (ER) positive DCIS and that of new breast primaries [5.6], its systemic effects have led to generally low acceptance in the DCIS and prevention setting [4-8]. These relate to estrogen agonist activity on the endometrium and the activation of coagulation pathways, leading to an increased risk of uterine events and thromboembolism [9]. Hot flashes and vaginal symptoms are an additional barrier to acceptance [7,10]. Thus a particular challenge for primary and secondary breast cancer prevention efforts is to devise an efficacious and nontoxic intervention which is likely to be widely accepted by women who will benefit from it.

One possible solution is transdermal delivery of active drugs through the skin envelope of the breast to achieve high local concentrations with low systemic exposure, exploiting the embryological origins of the breast as a skin appendage (a modified eccrine gland) with a well-developed internal lymphatic circulation [11]. Results from previous studies show that drugs applied to the breast skin are selectively concentrated in the breast [12,13], whereas drugs applied to the skin of other regions of the body penetrate the skin into the vascular system and are distributed systemically. Thus transdermal drug application to the breast skin can be considered as local transdermal therapy (LTT), a concept which is further reviewed elsewhere [14]. In previous studies, 4-hydroxytamoxifen (4-OHT) gel was applied to the breast skin in settings ranging from 2-3 weeks of pre-operative treatment in postmenopausal women with invasive cancer to treatment of mastalgia in premenopausal women for up to one year [12,13,15]. Since LTT is most suited to women with DCIS or those at high risk, we performed a pre-surgical randomized trial of LTT in women with DCIS, testing 4-OHT gel against oral-T. Here we report results from 26 evaluable subjects who completed the study prior to its closure due to expiration of the shelf-life of the 4-OHT gel, with no additional drug available.

Participants and Methods

Study Design.

Between November 2009 and March 2012, pre and post-menopausal women (age range 45-86) with a diagnosis of ER positive DCIS, (as defined in ASCO/CAP guidelines [16]) were recruited at Northwestern University and Washington University to a randomized, double-blind, placebo-controlled trial of LTT with 4-OHT gel versus oral-T during the window between diagnostic core needle biopsy and surgical excision (NCT00952731 or N01-CN-35157). Women at risk for thromboembolic disease were excluded, as were those with a history of exogenous hormone use within the past month, and tamoxifen or raloxifene use within the past two years. Randomization was stratified by menopausal status, and enrollment site. Initially, the FDA required exclusions for grade 3 and comedo-type DCIS, mammographic DCIS size of >5 cm, and palpable lesions; these were removed following enrollment of nine subjects in the first year.

Study Medication.

4-OHT gel (Besins Healthcare BHR Pharma, LLC) was formulated as 0.2% (w/v) gel containing 200 mg of 4-OHT (E:Z=1:1) in 100 mL of hydroalcoholic, fast-drying gel supplied in a metered-dose container that dispensed 1.0 mL of gel (2 mg of 4-OHT or placebo) with each pump. Oral-T (20 mg) and placebo capsules were supplied by NCI, Division of Cancer Prevention: (Z)-tamoxifen tablets in opaque gelatin capsules filled with microcrystalline cellulose powder.

Study Procedures.

All participants provided informed consent. Baseline assessments included a history and physical, explanation of gel application, completion of the Breast Cancer Prevention Trial Eight Symptom Scale (BESS) questionnaire [17], collection of a venous blood sample, and collection of nipple aspirate fluid (NAF) from NAF yielders [18]. Following randomization, study drug was shipped to participants: the gel group received 4-OHT gel (4 mg daily, 2 mg to each breast) and oral placebo; the oral group received tamoxifen capsules (20 mg daily) and placebo gel. Treatment began within 5 days post-randomization and ended on the day prior to surgical resection. Participants were instructed to apply the gel to the entire skin envelope of each breast each morning, after a shower. Duration of therapy was 6-10 weeks. Compliance was assessed through participant diaries, counts of returned pills and of returned gel canisters. Participants who took at least 80% of the prescribed dose were considered compliant.

Assessments similar to those performed at baseline were repeated on the day prior to, or on the morning of surgery. During surgery, breast adipose tissue from the surgical sample was snap frozen and stored at −80° C. for measurement of tamoxifen and metabolites. The samples were obtained from a location adjacent to the DCIS lesion to provide uniformity between participants undergoing breast conservation and mastectomy. The paraffin block of the core and excision samples were acquired by the recruiting institution and 10 sections from each specimen were submitted to the NU Pathology Core Facility. The sections were cut in batches (with pre- and post-treatment samples in the same batch), shipped cold, and processed for immunohistochemistry within four weeks.

The BESS Questionnaire was repeated at day 15 and at the end of treatment (1 day before surgery or day of surgery), and the post-surgical visit (approximately 7-14 days after surgery). In an independent assessment at the same time points, adverse events were coded using the NCI Common Terminology Criteria for Adverse Events (CTCAE) version 3.0.

Study Endpoints.

The primary efficacy endpoint of this study was to demonstrate that daily application of 4-OHT gel to the breasts results in a reduction in the Ki-67 labeling index (LI) of DCIS lesions, similar to that seen with oral-T, comparing the diagnostic core biopsy to the surgical excision sample. Secondary endpoints were 1) to compare concentrations of tamoxifen and its metabolites [4-OHT, endoxifen, N-desmethyl tamoxifen (NDT)] in breast tissue, plasma and NAF obtained on the day of surgery; 2) to assess changes in known tamoxifen modulated pathways in the breast (COX-2 and maspin protein expression, [19,20]) and plasma (SHBG, IGF-1 [14]). Side effect endpoints were 1) the incidence of hot flashes at baseline and before surgery; 2) changes in coagulation related proteins in women on the gel and the oral arms from baseline to immediately before surgery.

Ki-67, COX-2 and Maspin Expression.

Immunohistochemical (IHC) assessment of these markers was performed on paraffin embedded sections of the core and excision specimens, using standard IHC techniques and MCF7, HCT116 and H292 cells as controls. For maspin we used primary mouse monoclonal antibody (Clone-G167-70, BD Pharmingen, San Jose, Calif.), dilution 1:200; for COX-2, primary mouse monoclonal antibody (Clone-CX-294, Dako, Denmark), dilution 1:100-; and for Ki67, primary mouse monoclonal antibody (Clone-MIB-1, Dako, Denmark), dilution 1:100-antigen. Dako Envision Plus system HRP labeled polymer for 20 min at 37° C. was used as the detection system. Scoring was performed on DCIS lesions only, with manual counting of positively stained DCIS cells. The Ki67 LI was assessed on an average of 300 DCIS cells at 40× magnification. The H score system (Score range: 0-300) was used for COX-2 and maspin markers by a single observer who was blinded to treatment status, with random verification of 20% of slides by a pathologist (PK) [21].

Plasma and Breast Tissue Concentration Measurement of Tamoxifen and its Metabolites.

(Z)-tamoxifen, (Z)-NDT, (E) and (Z)-4-OHT, and (Z)-endoxifen were measured by liquid chromatography-tandem mass spectrometry with a turbo ion spray interface operating in positive mode (API 3000; AB SCIEX, Foster City, Calif.). Briefly, 100 µL of plasma was mixed with 200 µL of acetonitrile containing 1 ng each of the deuterated analogs of the analytes (TRC, Toronto, Canada), centrifuged at 4° C. and 7000 RPM for 10 minutes, and supernatant diluted with 200 µL of water before analysis. For analysis of NAF, samples were collected in a capillary tube and diluted with 200 µL of phosphate buffered saline; 100 µL of the diluted NAF sample was used for analysis. Breast adipose tissue samples, 25 mg, were minced and treated with 125 µL of a 1 mg/mL arsenic solution in 2% nitric acid (Inorganic Ventures, Christiansburg, Va.) and extracted as described above.

Chromatographic separation was achieved with a Kinetex PFP 2.6µ column, 50×2.1 mm (Phenomenex, Torrance, Calif.). The mobile phase was A: 0.1% formic acid in water (v/v) and B: 0.1% formic acid in acetonitrile (v/v). The flow rate was 0.3 ml/min at 25° C. Retention times for (Z)-tamoxifen, (Z)-NDT, (Z)-4-OHT, (E)-4-OHT and (Z)-endoxifen were 7.3, 6.8, 5.1, 4.7 and 4.5 min, respectively. Total run time was 13 min Acquisition was performed in multiple reaction monitoring mode using m/z 372.2→72.1, 388.2→72.1, 374.2→72.1 and 358.2→72.1 at low resolution for tamoxifen, 4-OHT, endoxifen and NDT, respectively. In three participants, matched samples were not available: breast adipose tissue was not collected in two, and the plasma sample was missing in one.

Since the fraction of E and Z isoforms of 4-OHT was of particular interest, we used an additional validated method to study plasma concentrations of these metabolites in a different laboratory (Eurofins Medinet, Chantilly, Va.): Plasma from blood samples collected in lithium-heparin tubes was frozen at −20° C., shipped in batches on dry ice to them Eurofins Medinet central laboratory; LC-MS/MS was used for the simultaneous determination of (E) 4-OHT and (Z) 4-OHT, with a lower limit of quantitation (LOQ) of 10 pg/mL and upper LOQ of 10,000 pg/mL. Eurofins Medinet developed and validated them method for BHR Pharma, in accordance with the FDA Guidance on Bioanalytical Method Validation [22].

Circulating Marker Assessment.

Plasma samples collected with anticoagulant K3-EDTA were used for human IGF-1 and SHBG assays, and coagulation protein assays (factor VIII, factor IX, von Willebrand factor, and protein S)[23]. The human IGF-1 and SHBG assays were performed with Quantikine Enzyme-linked immunosorbant assay (ELISA) Kits (R&D Systems, Cat# DG100 for IGF-1, and Cat# DSHBG0 for SHBG assay). The lower limit of detection was 56 pg/ml, and 5 pmol/L; % CV values were 4.3 and 5.6 for IGF-1, and SHBG assay, respectively. Factor VIII, and factor IX were determined with VisuLize™ antigen ELISA kits (Affinity Biologicals Inc.). von Willebrand factor was measured with immune-turbidimetric assay (Diagnostica Stago Inc.Cat#00518) by STAR analyzer, and total protein S was assayed with an ELISA kit (REAADSR Inc.)

Statistical Design and Analysis.

The study was powered to detect a 50% reduction in Ki67 LI from baseline to post-therapy, with the hypothesis that change would be similar in the two groups. Therefore, if the mean relative decrease in the 4-OHT group was at least 30%, this would be considered equivalent to a relative decrease of up to 50% in the tamoxifen group. With alpha=5% and beta=20%, the planned sample size was 112 women, expecting that 90 would be evaluable for the primary endpoint of Ki67 LI. The study was halted early, but our assumptions regarding relative variability in the data and relative change from baseline have held for the main variable. In particular, the baseline means for Ki67 are 8.3% and 6.7% in the oral and in the 4-OHT groups respectively, while the corresponding SDs are 5.2% and 5.6%. This gives the coefficients of variation of 5.2/8.3=0.63 which is exactly what we assumed for the oral group and 5.6/6.7=0.84 which is around 30% larger than what we assumed for the 4-OHT group.

For continuous variables in the immunochemistry, drug concentration, and blood coagulation data, means and standard deviations are reported; the significance of changes between baseline and post-treatment within groups were evaluated with the paired t-test, and differences between treatment groups assessed using the unpaired t-test. For categorized demographic data, we examined the association of these variables with treatment group via Fisher's exact test. For the analysis of quality of life, the 33 symptoms in the BESS Questionnaire were divided into eight clusters as described by Cella et. al. [17]. The mean score within each cluster was used to evaluate significance of changes from baseline to posttreatment within groups as well as the differences between treatment groups using the Wilcoxon signed-rank test.

Results

A total of 31 subjects were enrolled over 29 months (November 2009 to July 2011), at which point the shelf-life of the drug expired and the study was closed. Three participants were ineligible (two with ER negative DCIS, and one with high creatinine); one participant withdrew consent before randomization. Of 27 randomized participants, one was withdrawn from the study due to lack of drug supply. A total of 26 subjects completed the study, 14 in the oral-T group and 12 in the topical 4-OHT gel group (see FIG. 1). The range of therapy duration was 6-10 weeks and the median time on treatment was 6 weeks (see Table 1).

TABLE 1

Participant characteristics at baseline[1], DCIS size from surgical specimen, and the duration of treatment according to treatment groups

|  | Oral-T (20 mg/day) | 4-OHT gel (4 mg/day) | P |
|---|---|---|---|
| No. of participants | N = 14 | N = 12 |  |
| Age, years (IQR)* | 54 (50, 61) | 60 (52, 65) | 0.29 |
| Menopausal Stems |  |  |  |
| Pre | 3 (21.4%) | 4 (33.3%) | 0.67 |
| Post | 11 (78.6%) | 8 (66.7%) |  |
| Race |  |  |  |
| Caucasian | 6 (42.9%) | 7 (58.3%) | 0.70 |
| Non-Caucasian | 8 (57.1%) | 5 (41.7%) |  |
| DCIS grade |  |  |  |
| 1 | 3 (21.4%) | 1 (8.3%) | 0.69 |
| 2 | 10 (71.4%) | 9 (75.0%) |  |
| 3 | 1 (7.1%) | 2 (16.7%) |  |
| DCIS size at surgery, cm (IQR)* | 1.9 (0.6, 2.4) | 0.58 (0.4, 1.36) | 0.23 |
| % ER expression (IQR)* | 80% (67, 95) | 85% (67, 100) | 0.86 |
| % PR expression (IQR)* | 67% (26, 90) | 67% (33, 75) | 0.84 |
| Days of treatment (IQR)* | 44 (42, 47) | 46 (45, 48) | 0.29 |
| 40-59 days | 12 (85.7%) | 10 (83.3%) |  |
| 60-69 days | 2 (14.3%) | 2 (16.7%) |  |

[1]A total of 27 participants were randomized, but 26 participants completed the intervention.
*Values are reported in median with interquartile range (IQR)

Baseline Participant Characteristics.

Participant demographics and clinical characteristics according to treatment groups were not significantly different (see Table 1). In particular, there were no significant differences in DCIS grade, lesion size, ER and PR expression, age or menopausal status.

Tissue Markers.

We were not able to obtain matched core and excision samples from two participants. Another six participants were excluded from analysis of IHC endpoints because the DCIS lesion had been exhausted in the baseline sample in one, and there was insufficient DCIS remaining in the excision specimen in five additional participants. Thus, of 26 women completing the study, matched DCIS lesions from baseline and post-treatment specimens were not available on eight, yielding a total of 18 subjects who were evaluable for IHC markers (9 in the tamoxifen group, and 9 in the 4-OHT gel group). The changes in Ki-67 LI in DCIS lesions, according to the treatment group, are summarized in Table 2.

TABLE 2

Ki67, COX-2, and maspin changes according to the treatment groups

|  | Oral-T (20 mg/day) (N = 9) | | 4-OHT gel (4 mg/day) (N = 9) | | |
|---|---|---|---|---|---|
|  | Mean ± SD | P* | Mean ± SD | P* | P† |
| Ki-67 |  |  |  |  |  |
| baseline | 8.3 ± 5.2 |  | 6.7 ± 5.6 |  |  |
| post-treatment | 3.2 ± 2.3 |  | 3.2 ± 2.6 |  |  |
| Changes from baseline | −5.1 ± 5.5 | 0.008 | −3.4 ± 5.0 | 0.03 | 0.99 |

TABLE 2-continued

Ki67, COX-2, and maspin changes according to the treatment groups

|  | Oral-T (20 mg/day) (N = 9) | | 4-OHT gel (4 mg/day) (N = 9) | | |
|---|---|---|---|---|---|
|  | Mean ± SD | P* | Mean ± SD | P* | P† |
| COX-2 | | | | | |
| baseline | 67.2 ± 72.4 | | 53.9 ± 55.7 | | |
| post-treatment | 78.9 ± 63.5 | | 35.7 ± 28.9 | | |
| Changes from baseline | 11.7 ± 109.8 | 0.46 | −18.2 ± 32.2 | 0.44 | 0.19 |
| Maspin | | | | | |
| baseline | 107 ± 56 | | 120 ± 97 | | |
| post-treatment | 142 ± 69 | | 162 ± 37 | | |
| Changes from baseline | 35 ± 71 | 0.43 | 41 ± 115 | 0.23 | 0.38 |

Abbreviation:
DCIS = Ductal carcinoma in situ;
Cyclooxygenase-2 = COX-2.
Ki-67 LI was represented in %;
COX-2 and maspin in H-score.
*Paired t-test for changes from baseline within a treatment group.
†Unpaired t-test for changes from baseline between treatment groups.

The mean Ki-67 LI after the treatment decreased significantly from baseline in both treatment groups (mean reduction 5.1% in tamoxifen group, p=0.008 and 3.4% in the topical 4-OHT group, p=0.03. This mean reduction in the two groups was statistically similar (p=0.99). COX-2 and maspin changes by treatment are shown in Table 2. There were no significant differences between baseline and post-treatment in COX-2 or maspin expression within each treatment group. Also, no differences were noted between treatment groups with respect to the baseline-to-post-treatment changes in these biomarkers (p=0.19 for COX-2; p=0.38 for maspin).

Plasma and Tissue Concentrations of Tamoxifen and its Metabolites.

There were a total of 23 participants (13 treated with tamoxifen and 10 with 4-OHT gel) whose plasma and breast adipose tissue samples, matched pre- and post-treatment, were available for quantitation of tamoxifen and its metabolites (NDT, 4-OHT, and endoxifen). The mean plasma and tissue concentration of each analyte is reported in Table 3.

TABLE 3

Concentrations of tamoxifen and its metabolites in breast tissue (ng/g) and plasma (ng/mL)

| | Breast adipose tissue | | | Plasma | | |
|---|---|---|---|---|---|---|
| Analytes | Tamoxifen (20 mg/day) (N = 13) | 4-OHT gel (4 mg/day) (N = 10) | P* | Tamoxifen (20 mg/day) (N = 13) | 4-OHT gel (4 mg/day) (N = 10) | P* |
| (Z) Tamoxifen | 2959 ± 1035 | BQL | | 90 ± 45 | BQL | |
| (Z) NDT | 492 ± 192 | BQL | | 149 ± 57 | BQL | |
| (E) 4-OHT | BQL | 5.2 ± 10.0 | | BQL | BQL | |
| (Z) 4-OHT | 5.4 ± 2.8 | 5.8 ± 9.3 | 0.88 | 1.1 ± 0.7 | 0.2 ± 0.2 | 0.0003 |
| (Z) Endoxifen | 8.0 ± 6.8 | BQL | | 5.9 ± 3.2 | BQL | |
| Independent validation in Eurofins laboratory | | | | | | |
| (E) 4-OHT | | | | 0.010 ± 0.006 | 0.056 ± 0.072 | 0.06 |
| (Z) 4-OHT | | | | 1.488 ± 0.771 | 0.261 ± 0.284 | <0.0001 |

Abbreviation:
NDT = N-desmethyltamoxifen;
4-OHT = 4-hydroxytomoxifen;
Endoxifen = N-desmethyl 4-hydroxytamoxifen;
IQR = interquartile range;
BQL = below the lowest limit of quantification (LLOQ).

All the concentrations were reported as means ± standard deviation. Tissue concentration was represented in ng/g (LLOQ = 3 ng/g). (E) isomers of NDT, and Endoxifen were BQL. Plasma concentration was represented in ng/mL (LLOQ = 20 ng/mL for tamoxifen and NDT: 1 ng/mL for 4-OHT and Endoxifen). (E) isomers of NDT, 4-OHT, and Endoxifen were BQL.
LLOQ of plasma concentration measured by Eurofins laboratory was 10 pg/mL for both E and Z isomers.
*Unpaired t-test test between oral and topical treatment groups Detectable levels of tamoxifen, NDT and endoxifen were found only in the oral-T group, with mean values being substantially higher in tissue than in plasma. In contrast, (Z) 4-OHT was detectable in the tissue of both oral and gel groups, at equivalent concentrations (5.4 ng/g and 5.8 ng/g, respectively, p=0.88), while plasma concentrations were markedly different (1.1 ng/mL in the oral-T group and 0.2 ng/mL in the 4-OHT gel group, p=0.0003 (see Table 3). (E) 4-OHT was present in breast adipose tissue of the gel group at a concentration of 5.2±10.0 ng/g. Data on plasma (Z) 4-OHT concentrations from both laboratories were very similar, but the (E) 4-OHT assay was more sensitive in the Eurofins laboratory, and (E) 4-OHT was detectable in plasma of both gel and oral groups, at levels that were considerably lower than those of (Z) 4-OHT (see Table 3).

Overall, we found that 4-OHT was detectable in breast tissue for 9 of 10 participants in the 4-OHT gel group for whom samples were available; and in plasma for 5 participants. We observed a direct correlation between plasma and tissue concentration of (Z) 4-OHT in the oral-T group (Spearman correlation coefficient=0.79, p=0.0007); however there was no such correlation in the 4-OHT gel group (Spearman correlation coefficient=0.24, p=0.48). We then looked at individuals with the highest (Z) 4-OHT tissue concentrations (>1.5-fold of the mean); in the 4-OHT gel treated group, there were two such participants, with 14.9 ng/g and 33.2 ng/g of (Z) 4-OHT in breast. However their plasma (Z) 4-OHT was undetectable for one participant, and 0.22 ng/mL for the other, compared to the mean (0.2 ng/mL).

Drug Concentrations in NAF.

We obtained post-treatment NAF (3 µL to 40 µL) from the contralateral breast of six participants, and were able to detect tamoxifen or its metabolites in NAF samples of four participants, two in the tamoxifen and two in the 4-OHT gel group. In the oral-T group, NAF concentrations of tamoxifen and NDT were higher than the plasma concentrations (participant A: 320 vs. 94.3 ng/mL for tamoxifen, and 406 vs. 133 ng/mL for NDT; participant B: 182 vs. 160 ng/mL for tamoxifen, and 355 vs. 222 ng/mL for NDT) whereas 4-OHT and endoxifen were undetectable. In the 4-OHT gel group, tamoxifen, NDT, and endoxifen were undetectable, but both isomers of 4-OHT were detected in similar amounts, with (Z) 4-OHT concentration >40 fold higher than the plasma concentration (participant C: 16.7 vs. 0.42 ng/mL; participant D: 25.1 ng/mL vs. BQL. Of the two NAF samples with undetectable tamoxifen or metabolites, one subject received oral-T, had detectable plasma tamoxifen (54 ng/mL) and NDT (136 ng/mL), but unfortunately no breast tissue sample was collected for drug quantitation at surgery. The other subject with undetectable tamoxifen or metabolites in NAF received active 4-OHT gel, and had a high breast adipose tissue 4-OHT level of 33.2 ng/g for (Z) 4-OHT.

Tamoxifen Responsive-Circulating Markers.

Mean baseline IGF-1, SHBG, vWF, factor VIII, factor IX, and total protein S levels are shown in Table 4.

TABLE 4

Changes in circulating markers according to the treatments

| | Tamoxifen (20 mg/day) (N = 13) | | 4-OHT gel (4 mg/day) (N = 10) | | |
|---|---|---|---|---|---|
| | Mean ± SD | P* | Mean ± SD | P* | P† |
| IGF-1 (ng/mL) | | | | | |
| baseline | 59.0 ± 11.4 | | 63.7 ± 8.6 | | |
| post-treatment | 50.3 ± 9.7 | | 58.5 ± 6.6 | | |
| Changes from baseline | −8.7 ± 8.3 | 0.003 | −5.2 ± 9.5 | 0.12 | 9.35 |
| SHBG (ng/mL) | | | | | |
| baseline | 98.4 ± 45.0 | | 89.4 ± 70.2 | | |
| post-treatment | 143.9 ± 69.0 | | 99.7 ± 76.0 | | |
| Changes from baseline | 45.5 ± 40.2 | 0.002 | 10.3 ± 74.4 | 0.67 | 0.20 |
| % vWF | | | | | |
| baseline | 167.4 ± 89.2 | | 179.9 ± 68.3 | | |
| post-treatment | 218.6 ± 134.6 | | 177.3 ± 65.3 | | |
| Changes from baseline | 51.2 ± 71.0 | 0.02 | −2.6 ± 52.3 | 0.88 | 0.06 |
| % Factor VIII | | | | | |
| baseline | 157.1 ± 47.5 | | 158.4 ± 23.4 | | |
| post-treatment | 168.7 ± 51.6 | | 167.1 ± 24.5 | | |
| Changes from baseline | 11.6 ± 17.3 | 0.03 | 8.7 ± 18.5 | 0.17 | 0.70 |
| % Factor IX | | | | | |
| baseline | 86.6 ± 8.8 | | 86.7 ± 7.0 | | |
| post-treatment | 87.0 ± 12.2 | | 81.1 ± 12.7 | | |
| Changes from baseline | 0.4 ± 10.2 | 0.89 | −5.6 ± 13.6 | 0.22 | 9.24 |
| % Total Protein S | | | | | |
| baseline | 94.3 ± 8.9 | | 97.5 ± 7.0 | | |
| post-treatment | 91.6 ± 12.2 | | 95.9 ± 9.2 | | |
| Changes from baseline | −2.7 ± 9.3 | 0.32 | −1.6 ± 6.5 | 0.46 | 0.76 |

Abbreviation:
IGF-1 = insulin-like growth factor-1:
SHBG = sex hormone-binding globulin;
vWF = von Willebrand factor.
*Paired t-rest between baseline and post-treatment value within a treatment group
†Unpaired t-test for changes from baseline between treatment groups.

Overall, these markers of systemic hormonal effects were induced in the tamoxifen group, but not in the 4-OHT group. Specifically, median SHBG levels increased significantly following tamoxifen therapy (p=0.002), but not with 4-OHT gel therapy (p=0.67). Mean vWF and factor VIII levels increased significantly with oral-T therapy (p=0.02 and p=0.03, respectively) but not with 4-OHT gel therapy (p=0.88, and p=0.17, respectively). The mean levels of factor IX and total protein S did not change for either treatment group. Finally, mean IGF-1 levels were significantly lower than baseline in the oral-T group (p=0.003), but not in the 4-OHT gel group. However, between-group comparisons of these treatment-related changes did not reach statistical significance.

Quality of Life Assessment.

Quality of life parameters assessed by BESS questionnaire are summarized in Table 5.

TABLE 5

Summary of BESS Quality of Life Assessment by symptom clusters according to the treatments

| Symptom Cluster | Tamoxifen (20 mg/day) (N = 14) | | 4-OHT gel (4 mg/day) (N = 12) | | |
|---|---|---|---|---|---|
| | Mean ± SD | P* | Mean ± SD | P* | P† |
| Cognitive | | | | | |
| baseline | 0.62 ± 0.61 | | 0.61 ± 1.11 | | 0.54 |
| post-treatment | 0.71 ± 1.18 | | 0.69 ± 1.20 | | |
| Changes from baseline | 0.10 ± 0.86 | 0.99 | 0.08 ± 0.47 | 0.81 | 0.64 |
| Body pain | | | | | |
| baseline | 0.76 ± 1.12 | | 0.56 ± 0.94 | | 0.49 |
| post-treatment | 1.19 ± 1.11 | | 0.58 ± 0.74 | | |
| Changes from baseline | 0.43 ± 0.92 | 0.11 | 0.03 ± 0.61 | 0.78 | 0.27 |
| Vasomotor | | | | | |
| baseline | 0.33 ± 0.45 | | 0.19 ± 0.41 | | 0.35 |
| post-treatment | 0.88 ± 1.26 | | 0.53 ± 0.73 | | |
| Changes from baseline | 0.55 ± 1.05 | 0.06 | 0.33 ± 0.64 | 0.13 | 0.83 |
| Gastrointestinal | | | | | |
| baseline | 0.12 ± 0.31 | | 0.00 ± 0.00 | | 0.18 |
| post-treatment | 0.02 ± 0.09 | | 0.06 ± 0.13 | | |
| Changes from baseline | −0.10 ± 0.24 | 0.50 | 0.06 ± 0.13 | 0.50 | 0.049 |
| Sexual problems | | | | | |
| baseline | 0.32 ± 0.72 | | 0.42 ± 0.67 | | 0.55 |
| post-treatment | 0.11 ± 0.40 | | 0.25 ± 0.5 | | |
| Changes from baseline | −0.21 ± 0.54 | 0.25 | −0.17 ± 0.81 | 0.53 | 0.48 |
| Bladder | | | | | |
| baseline | 0.14 ± 0.36 | | 0.17 ± 0.39 | | 0.87 |
| post-treatment | 0.25 ± 0.33 | | 0.25 ± 0.40 | | |
| Changes from baseline | 0.11 ± 0.49 | 0.59 | 0.08 ± 0.19 | 0.50 | 0.67 |
| Body image | | | | | |
| baseline | 0.68 ± 0.77 | | 0.63 ± 0.83 | | 0.55 |
| post-treatment | 0.64 ± 0.89 | | 0.75 ± 1.06 | | |
| Changes from baseline | −0.04 ± 0.87 | 0.92 | 0.13 ± 0.53 | 0.75 | 0.26 |
| Vaginal | | | | | |
| baseline | 0.00 ± 0.00 | | 0.14 ± 0.26 | | 0.052 |
| post-treatment | 0.07 ± 0.19 | | 0.14 ± 0.33 | | |
| Changes from baseline | 0.07 ± 0.19 | 0.50 | 0.00 ± 0.14 | 0.75 | 0.08 |

*Wilcoxon signed-rank tests were used for the changes from baseline within a treatment group.
†Wilcoxon rank-sum tests were used for baseline, and the changes from baseline between treatment groups.

At baseline, the mean scores for all clusters were similar for the two treatment groups, with the exception of the vaginal symptom cluster which was marginally higher in the 4-OHT gel group (0.14 compared to 0.00, p=0.052) Following treatment, the mean score for vasomotor symptoms (hot flashes, night sweats, and cold sweats) increased slightly compared to baseline in both groups (oral-T p=0.06 and 4-OHT gel group p=0.13), but, these changes were not significantly different between the two treatment groups (p=0.83). The gastrointestinal symptom cluster score was somewhat higher in the oral-T group at baseline, and although the within-group change was not significant in either oral or transdermal groups, the between group comparison did reach statistical significance (p=0.049). There were no other between-group differences in the change of symptom severity from baseline to post-treatment. In addition, in our collection of CTCAE data, no serious adverse events were reported in this study.

Discussion

Local transdermal therapy (LTT) to the breast for prevention of in-breast recurrence of DCIS and occurrence of new primary tumors is a promising approach with the potential of significantly reducing side effects through reduced systemic exposure. We report the first study of this approach in women with DCIS, comparing a proven breast cancer prevention agent (tamoxifen) given orally, and one of its active metabolites (4-hydroxytamoxifen) given transdermally to the breast for at least 6 weeks. Although we did not reach our target accrual, we report results on the crucial issue of drug concentration in blood and plasma, and preliminary data on biomarkers of efficacy (Ki67 labeling in DCIS tissue) and systemic exposure (plasma levels of IGF-1, SHBG, and coagulation proteins).

Our primary endpoint was Ki-67 LI, which is the best validated and most widely accepted endpoint for window-of-opportunity studies of systemic agents for breast cancer [24]. Encouragingly, although the power of our study to 'prove' equivalence between groups is limited since only 28% of the subjects were accrued, our assumptions regarding variability in Ki67-LI and relative change from baseline have held, in that the baseline means for Ki67-LI in the two groups and the corresponding SDs and coefficients of variation are very close to the assumptions used for the statistical plan. The drop in Ki67-LI was larger than anticipated in both groups: 61% rather than 50% in the oral group, and 52% rather than 30% in the 4-OHT group, consistent with the projected 'effect size'. Our findings are strengthened by an earlier study of postmenopausal women with ER positive invasive cancers, where 2-3 weeks of treatment with up to 2 mg of 4-OHT gel (1 mg per breast) was compared to oral-T prior to cancer resection; cell proliferation decreased to a similar degree with oral and transdermal therapy, and 4-OHT plasma concentrations were significantly lower in the transdermal group [13]. In contrast, we included pre and postmenopausal women, used a higher daily dose of 4-OHT (4 mg) and a longer treatment interval of 6-10 weeks to allow an assessment of vasomotor symptoms.

We assessed COX-2 and maspin labeling of DCIS lesions because of previous evidence that their expression is modulated by tamoxifen[25][19] Although significant modulation in COX-2 and maspin expression was not seen in either group, these potential markers of DCIS biology remain of interest [20,26].

Our results support the hypothesis that effective breast concentrations can be achieved with low systemic exposure; the breast adipose tissue concentrations of (Z) 4-OHT were equivalent in the oral and LTT groups (over 5 ng/mg tissue in both groups). Our results compare favorably with the previous study where median 4-OHT concentration in non-tumor breast tissue was 2.0 ng/g in the oral-T group and 0.8 ng/g in the 4-OHT gel group (2 mg daily) [13]. In contrast, the mean plasma level of 4-OHT was more than five-fold lower in the 4-OHT gel group than in the tamoxifen group using two independent methods in different laboratories. Although data on NAF concentrations were available on only four women, these too support the main finding of high mammary concentrations of 4-OHT achieved with LTT, and are of interest because they imply a within-breast distribution of the drug that allows high concentrations to appear in nipple fluid. Thus our pharmacokinetic results compare favorably with previous reports and suggest that LTT for breast cancer prevention and for DCIS therapy using 4-OHT gel should be effective; a reduction in long term side effects remains to be demonstrated; nevertheless, the data are encouraging and support the design of future studies.

We measured 4-OHT isomers since they differ in anti-estrogenic activity, with the (Z) isomer of 4-OHT and endoxifen being the major biologically active forms [27-29]. The pure (Z) form is difficult to stabilize in the manufacturing process, and 4-OHT gel contains equal amounts of both isomers. We found that the concentrations of 4-OHT isomers were similar in breast adipose tissue in the oral and gel groups, whereas plasma concentrations were significantly lower in the gel group, with no evidence of isomerization (Z→E) (Table 3). This contrasts with the result from an earlier topical study using 3H labeled (Z) 4-OHT to the breasts [30], where the authors reported a progressive (Z→E) isomeriza on in breast tissue samples collected from 12 h to day 7. Other topical 4-OHT gel studies reported total concentration of 4-OHT rather than concentration of each isomer [12,13,15]. In agreement with previous studies [12, 13,15], we did not see any further metabolic transformation of 4-OHT to endoxifen in the breast adipose tissue following topical 4-OHT gel administration.

Recently, endoxifen has attracted attention based on its greater abundance relative to 4-OHT in women on oral-T [31,32], and a report that endoxifen causes proteosomic degradation of ERα and may have more selective anti-estrogenic effects [33]. We found marginally higher concentrations of endoxifen than 4-OHT in the breast adipose tissue of the oral-T group, and it is possible that the combined presence of endoxifen and 4-OHT implies better efficacy. However, it remains reassuring that the magnitude of the post-therapy Ki67 decrease was similar in the oral and gel groups. Endoxifen and 4-OHT have equal binding affinity for the ER [34,35], and in vitro transdermal permeability [36]; future studies using a gel formulation of endoxifen would therefore be of interest.

Tamoxifen has been reported to affect plasma levels of IGF-1 and SHBG [37-39], providing a measure of the pharmacologic action of tamoxifen upon the hormone axis. Previous reports document a decrease in plasma IGF-I levels with tamoxifen therapy [37] and an increase in serum SHBG related to the estrogenic effect on the liver [38,39], which is dose dependent [40]. We observed significant decreases in IGF-1 and increases in SHBG in the tamoxifen group, but not in the 4-OHT gel group, supporting the notion that systemic effects of 4-OHT gel are small, if any. However, given the small sample sizes, the magnitude of the change was not statistically different between groups.

Similarly, the use of oral-T has been associated with changes in coagulation proteins such as von Willebrand factor (vWF), factor VIII, factor IX, and total protein S [12,40,41]. We found that the post-treatment levels of factor VIII and vWF were significantly increased post-therapy in the tamoxifen but not in the 4-OHT gel group. Thus, the avoidance of first-pass metabolism of tamoxifen in the liver potentially avoids changes in the clotting cascade that contribute to the pro-thrombotic effects of SERMS [42-44], a clear advantage.

Another significant adverse effect of SERM therapy relates to the induction of hot flashes, in both pre and postmenopausal women. The very low plasma concentrations observed following transdermal application of 4-OHT raises the possibility that hot flashes will be reduced by LTT with active tamoxifen metabolites [12,15,45]. However, the lowest plasma level of tamoxifen metabolite exposure to cause hot flashes has not been defined, and it is possible that even low-level exposure may be sufficient to cause hot flashes. We did not observe a significant effect on hot flash frequency following a minimum of six weeks of therapy, although our data is clearly limited by small numbers.

Finally, population variation in the efficiency of tamoxifen metabolism, related to polymorphisms in the CYP2D6 and other genes [46] may adversely affect efficacy of orally administered tamoxifen. LTT with an active tamoxifen metabolite circumvents the need for prodrug activation, potentially avoiding one source of low bioavailability of active [31,32]. Our finding supports this notion since topical gel application of 4-OHT achieved the similar breast concentration of 4-OHT compared to oral administration of tamoxifen.

An important question with transdermal delivery to the breast pertains to whether this is local therapy (higher concentrations in the breast than elsewhere) or systemic therapy (with similar concentrations throughout the body). Previous work has shown that 4-OHT applied to the breast skin results in 10-fold higher breast tumor levels than when it is applied to the arm or shoulder [12]. Although this differential accumulation was attributed to the binding of 4-OHT to ERs present in the breast, receptor binding alone is insufficient to explain 4-OHT retention at the levels observed [47,48]. A more likely explanation relates to the embryological origin of the breast as a skin appendage (i.e. a modified eccrine gland), so that the breast parenchyma and its skin envelope are a single unit with a well-developed internal lymphatic circulation [11], further evidenced by that fact that the skin and parenchyma of the breast drain to the same sentinel lymph nodes [49,50]. If breast retention of locally applied drugs is an anatomic rather than physiologic phenomenon, it predicts that other drugs applied to the skin of the breast should also concentrate in the parenchyma to a greater degree than can be expected based on transdermal systemic delivery through the circulation. Thus LTT may be applicable to a variety of agents as long as they are effective prevention agents and show sufficient dermal permeation.

Our trial was slow to accrue, particularly in the beginning. Few window-of-opportunity trials have been performed in women with DCIS, and despite the consensus among physicians that a surgical delay of six weeks was not risky, the majority of eligible subjects were unwilling to experience this delay. Furthermore, initially restrictive eligibility criteria, designed to minimize the likelihood that participants with a core biopsy showing DCIS had undiagnosed invasive disease, greatly decreased the pool of available subjects, and resulted in the recruitment of women with very small DCIS lesions, leading to an attrition of almost 30% in the assessment of biomarkers in matched pre- and post-therapy lesions. Ultimately, slow accrual led to expiration of the study agent, and a decision by the manufacturer to not produce additional supplies. In future studies, it is clear that enrollment criteria should be as open as possible.

In summary, our data support the notion that local transdermal drug delivery to the breast will achieve sufficient drug concentrations to be effective, with low systemic exposure. This concept deserves further testing with 4-OHT, and is likely to be applicable to other lipophilic drugs with low molecular weight.

REFERENCE LIST

1. Weaver D L, Rosenberg R D, Barlow W E, Ichikawa L, Carney P A, Kerlikowske K, et al. Pathologic findings from the Breast Cancer Surveillance Consortium: population-based outcomes in women undergoing biopsy after screening mammography. Cancer. 2006; 106:732-742. [PubMed: 16411214]
2. Ward E, Desantis C, Robbins A, Kohler B, Jemal A. Childhood and adolescent cancer statistics, 2014. C A Cancer J Clin. 2014
3. Fisher B, Dignam J, Wolmark N, Wickerham D L, Fisher E R, Mamounas E, et al. Tamoxifen in treatment of intraductal breast cancer: National Surgical Adjuvant Breast and Bowel Project B-24 randomised controlled trial. Lancet. 1999; 353:1993-2000. [PubMed: 10376613]
4. Wapnir I L, Dignam J J, Fisher B, Mamounas E P, Anderson S J, Julian T B, et al. Long-term outcomes of invasive ipsilateral breast tumor recurrences after lumpectomy in NSABP B-17 and B-24 randomized clinical trials for DCIS. J Natl Cancer Inst. 2011; 103:478-488. [PubMed: 21398619]
5. Tchou J, Hou N, Rademaker A, Jordan V C, Morrow M. Acceptance of tamoxifen chemoprevention by physicians and women at risk. Cancer. 2004; 100:1800-1806. [PubMed: 15112259]
6. Yen T W, Hunt K K, Mirza N Q, Thomas E S, Singletary S E, Babiera G V, et al. Physician recommendations regarding tamoxifen and patient utilization of tamoxifen after surgery for ductal carcinoma in situ. Cancer. 2004; 100:942-949. [PubMed: 14983489]
7. Port E R, Montgomery L L, Heerdt A S, Borgen P I. Patient reluctance toward tamoxifen use for breast cancer primary prevention. Ann Surg Oncol. 2001; 8:580-585. [PubMed: 11508619]
8. Melnikow J, Paterniti D, Azari R, Kuenneth C, Birch S, Kuppermann M, et al. Preferences of Women Evaluating Risks of Tamoxifen (POWER) study of preferences for tamoxifen for breast cancer risk reduction. Cancer. 2005; 103:1996-2005. [PubMed: 15825209]
9. Fisher B, Costantino J P, Wickerham D L, Redmond C K, Kavanah M, Cronin W M, et al. Tamoxifen for prevention of breast cancer: Report of the National Surgical Adjuvant Breast and Bowel Project P-1 Study. J Natl Cancer Inst. 1998; 90:1371-1388. [PubMed: 9747868]
10. Day R, Ganz P A, Costantino J, Cronin W M, Wickerham D L, Fisher B. Health-Related Quality of Life and Tamoxifen in Breast Cancer Prevention: A Report From the National Adjuvant Breast and Bowel Project P-1 Study. J Surg Oncol 9 A.D. 17:2659-2669.
11. Ackerman A B, Kessler G, Gyorfi T, Tsou H C, Gottlieb G J. Contrary view: the breast is not an organ per se, but a distinctive region of skin and subcutaneous tissue. Am J Dermatopathol. 2007; 29:211-218. [PubMed: 17414452]
12. Pujol H, Girault J, Rouanet P, Fournier S, Grenier J, Simony J, et al. Phase I study of percutaneous 4-hydroxy-tamoxifen with analyses of 4-hydroxy-tamoxifen concentrations in breast cancer and normal breast tissue. Cancer Chemother Pharmacol. 1995; 36:493-498. [PubMed: 7554041]
13. Rouanet P, Linares-Cruz G, Dravet F, Poujol S, Gourgou S, Simony-Lafontaine J, et al. Neoadjuvant percutaneous 4-hydroxytamoxifen decreases breast tumoral cell proliferation: a prospective controlled randomized study comparing three doses of 4-hydroxytamoxifen gel to oral tamoxifen. J Clin Oncol. 2005; 23:2980-2987. [PubMed: 15860853]
14. Lazzeroni M, Serrano D, Dunn B K, Heckman-Stoddard B M, Lee O, Khan S, et al. Oral low dose and topical tamoxifen for breast cancer prevention: modern approaches for an old drug. Breast Cancer Res. 2012; 14:214. [PubMed: 23106852]
15. Mansel R, Goyal A, Nestour E L, Masini-Eteve V, O'Connell K. A phase II trial of Afimoxifene (4-hydroxytamoxifen gel) for cyclical mastalgia in premenopausal women. Breast Cancer Res Treat. 2007; 106:389-397. [PubMed: 17351746]
16. Hammond M E, Hayes D F, Dowsett M, Allred D C, Hagerty K L, Badve S, et al. American Society of Clinical Oncology/College of American Pathologists guideline recommendations for immunohistochemical testing of estrogen and progesterone receptors in breast cancer (unabridged version). Arch Pathol Lab Med. 2010; 134: e48-e72. [PubMed: 20586616]
17. Cella D, Land S R, Chang C H, Day R, Costantino J P, Wolmark N, et al. Symptom measurement in the Breast Cancer Prevention Trial (BCPT) (P-1): psychometric properties of a new measure of symptoms for midlife women. Breast Cancer Res Treat. 2008; 109:515-526. [PubMed: 17851765]
18. Chatterton R T Jr. Khan S A, Heinz R, Ivancic D, Lee O. Patterns of sex steroid hormones in nipple aspirate fluid during the menstrual cycle and after menopause in relation to serum concentrations. Cancer Epidemiol Biomarkers Prev. 2010; 19:275-279. [PubMed: 20056648]
19. Liu Z, Shi H Y, Nawaz Z, Zhang M. Tamoxifen induces the expression of maspin through estrogen receptor-alpha. Cancer Lett. 2004; 209:55-65. [PubMed: 15145521]
20. Boland G P, Butt I S, Prasad R, Knox W F, Bundred N J. COX-2 expression is associated with an aggressive phenotype in ductal carcinoma in situ. Br J Cancer. 2004; 90:423-429. [PubMed: 14735188]
21. Wynes M W, Konopa K, Singh S, Reyna-Asuncion B, Ranger-Moore J, Sternau A, et al. Thymidylate synthase protein expression by IHC and gene copy number by SISH correlate and show great variability in non-small cell lung cancer. J Thorac Oncol. 2012; 7:982-992. [PubMed: 22551903]
22. CDER. Guidance for the Industry. Bioanalytical Method Validation. U.S. Department of Health and Human Services, Food and Drug Administration, Center for Drug Evaluation and Research and Center for Veterinary Medicine (CVM). 2001. Ref Type: Report
23. Green D, McMahon B, Foiles N, Tian L. Measurement of hemostatic factors in EDTA plasma. Am J Clin Pathol. 2008; 130:811-815. [PubMed: 18854275]
24. Dowsett M, Smith I, Robertson J, Robison L, Pinhel I, Johnson L, et al. Endocrine therapy, new biologicals, and new study designs for presurgical studies in breast cancer. J Natl Cancer Inst Monogr. 2011; 2011:120-123. [PubMed: 22043057]
25. Barker S, Malouitre S D, Glover H R, Puddefoot J R, Vinson G P. Comparison of effects of 4-hydroxy tamoxifen and trilostane on oestrogen-regulated gene expression in MCF-7 cells: upregulation of oestrogen receptor beta. J Steroid Biochem Mol Biol. 2006; 100:141-151. [PubMed: 16806905]
26. Umekita Y, Yoshida H. Expression of maspin is up-regulated during the progression of mammary ductal carcinoma. Histopathology. 2003; 42:541-545. [PubMed: 12786889]
27. Allen K E, Clark E R, Jordan V C. Evidence for the metabolic activation of non-steroidal antioestrogens: a study of structure-activity relationships. Br J Pharmacol. 1980; 71:83-91. [PubMed: 7470748]

28. Borgna J L, Rochefort H. Hydroxylated metabolites of tamoxifen are formed in vivo and bound to estrogen receptor in target tissues. J Biol Chem. 1981; 256:859-868. [PubMed: 7451477]
29. Robertson D W, Katzenellenbogen J A, Long D J, Rorke E A, Katzenellenbogen B S. Tamoxifen antiestrogens. A comparison of the activity, pharmacokinetics, and metabolic activation of the cis and trans isomers of tamoxifen. J Steroid Biochem. 1982; 16:1-13.
30. Mauvais-Javis P, Baudot N, Castaigne D, Banzet P, Kuttenn F. trans-4-Hydroxytamoxifen concentration and metabolism after local percutaneous administration to human breast. Cancer Res. 1986; 46:1521-1525. [PubMed: 3943109]
31. Goetz M P, Rae J M, Suman V J, Safgren S L, Ames M M, Visscher D W, et al. Pharmacogenetics of tamoxifen biotransformation is associated with clinical outcomes of efficacy and hot flashes. J Clin Oncol. 2005; 23:9312-9318. [PubMed: 16361630]
32. Goetz M P, Knox S K, Suman V J, Rae J M, Safgren S L, Ames M M, et al. The impact of cytochrome P450 2D6 metabolism in women receiving adjuvant tamoxifen. Breast Cancer Res Treat. 2007; 101:113-121. [PubMed: 17115111]
33. Wu X, Hawse J R, Subramaniam M, Goetz M P, Ingle J N, Spelsberg T C. The tamoxifen metabolite, endoxifen, is a potent antiestrogen that targets estrogen receptor alpha for degradation in breast cancer cells. Cancer Res. 2009; 69:1722-1727. [PubMed: 19244106]
34. Lim Y C, Desta Z, Flockhart D A, Skaar T C. Endoxifen (4-hydroxy-N-desmethyltamoxifen) has anti-estrogenic effects in breast cancer cells with potency similar to 4-hydroxy-tamoxifen. Cancer Chemother Pharmacol. 2005; 55:471-478. [PubMed: 15685451]
35. Lim Y C, Li L, Desta Z, Zhao Q, Rae J M, Flockhart D A, et al. Endoxifen, a secondary metabolite of tamoxifen, and 4-OH-tamoxifen induce similar changes in global gene expression patterns in MCF-7 breast cancer cells. J Pharmacol Exp Ther. 2006; 318:503-512. [PubMed: 16690721]
36. Lee O, Ivancic D, Chatterton R T, Rademaker A, Khan S A. In vitro human skin permeation of endoxifen: potential for local transdermal therapy for primary prevention and carcinoma in situ of the breast. Breast Cancer: Targets and Therapy. 2011; 3:61-70.
37. Lonning P E, Lien E A, Lundgren S, Kvinnsland S. Clinical pharmacokinetics of endocrine agents used in advanced breast cancer. Clin Pharmacokinet. 1992; 22:327-358. [PubMed: 1505141]
38. Kisanga E R, Gjerde J, Guerrieri-Gonzaga A, Pigatto F, Pesci-Feltri A, Robertson C, et al. Tamoxifen and metabolite concentrations in serum and breast cancer tissue during three dose regimens in a randomized preoperative trial. Clin Cancer Res. 2004; 10:2336-2343. [PubMed: 15073109]
39. Ellmen J, Hakulinen P, Partanen A, Hayes D F. Estrogenic effects of toremifene and tamoxifen in postmenopausal breast cancer patients. Breast Cancer Res Treat. 2003; 82:103-111. [PubMed: 14692654]
40. Decensi A, Robertson C, Viale G, Pigatto F, Johansson H, Kisanga E R, et al. A randomized trial of low-dose tamoxifen on breast cancer proliferation and blood estrogenic biomarkers. J Natl Cancer Inst. 2003; 95:779-790. [PubMed: 12783932]
41. Cosman F, Baz-Hecht M, Cushman M, Vardy M D, Cruz J D, Nieves J W, et al. Short-term effects of estrogen, tamoxifen and raloxifene on hemostasis: a randomized-controlled study and review of the literature. Thromb Res. 2005; 116:1-13. [PubMed: 15850603]
42. Cuzick J, Powles T, Veronesi U, Forbes J, Edwards R, Ashley S, et al. Overview of the main outcomes in breast-cancer prevention trials. Lancet. 2003; 361:296-300. [PubMed: 12559863]
43. Cosman F, Baz-Hecht M, Cushman M, Vardy M D, Cruz J D, Nieves J W, et al. Short-term effects of estrogen, tamoxifen and raloxifene on hemostasis: a randomized-controlled study and review of the literature. Thromb Res. 2005; 116:1-13. [PubMed: 15850603]
44. Cuzick J, Forbes J, Edwards R, Baum M, Cawthorn S, Coates A, et al. First results from the International Breast Cancer Intervention Study (IBIS-I): a randomised prevention trial. Lancet. 2002; 360:817-824. [PubMed: 12243915]
45. Mauvais-Javis P, Baudot N, Castaigne D, Banzet P, Kuttenn F. trans-4-Hydroxytamoxifen concentration and metabolism after local percutaneous administration to human breast. Cancer Research. 1986; 46(3):1521-5. [PubMed: 3943109]
46. Schroth W, Goetz M P, Hamann U, Fasching P A, Schmidt M, Winter S, et al. Association between CYP2D6 polymorphisms and outcomes among women with early stage breast cancer treated with tamoxifen. JAMA. 2009; 302:1429-1436. [PubMed: 19809024]
47. Khan S A, Rogers M A, Khurana K K, Meguid M M, Numann P J. Estrogen receptor expression in benign breast epithelium and breast cancer risk [see comments]. J Natl Cancer Inst. 1998; 90:37-42. [PubMed: 9428781]
48. Ricketts D, Turnbull L, Ryall G, Bakhshi R, Rawson N S B, Gazet J C, et al. Estrogen and progesterone receptors in the normal female breast. Cancer Res. 1991; 51:1817-1822. [PubMed: 2004366]
49. Povoski S P, Olsen J O, Young D C, Clarke J, Burak W E, Walker M J, et al. Prospective Randomized trial comparing intradermal, intraparenchymal, and subareolar injection routes for sentinel lymph node mapping and biopsy in breast cancer. Ann Surg Oncol. 2006; 13:10-11. [PubMed: 16372150]
50. Klimberg V S, Rubio I T, Henry R, Cowan C, Colvert M, Korourian S. Subareolar versus peritumoral injection for location of the sentinel lymph node. Ann Surg. 1999; 229:860-864. [PubMed: 10363900]

Example 2

Reference is made to Lee et al., "Local transdermal therapy to the breast for breast cancer prevention and DCIS therapy: preclinical and clinical evaluation," Cancer Chemother. Pharmacol. DOI 10.1007/s00280-015-2848-y, published online: 11 Nov. 2015, the content of which is incorporated by reference in the application in its entirety.

Abstract

Purpose.

Women at high risk of breast cancer and those with carcinoma in situ need non-toxic, well-tolerated preventive interventions. One promising approach is drug delivery through the breast skin (local transdermal therapy, LTT). Our goal was to test novel drugs for LTT, to establish that LTT is applicable to non-steroidal drugs.

Methods.

Athymic nude rats were treated with oral tamoxifen, transdermal 4-hydroxytamoxifen (4-OHT) or endoxifen gel applied daily to the axillary mammary gland for 6 weeks (Study 1). Study 2 was identical to Study 1, testing transdermal telapristone acetate (telapristone) gel versus subcutaneous implant. At euthanasia, mammary glands and blood were collected. In Study 3, consenting women requiring mastectomy were randomized to diclofenac patch applied to the abdomen or the breast for 3 days preoperatively. At surgery, eight tissue samples per breast were collected from predetermined locations, along with venous blood. Drug concentrations were measured using liquid chromatography-tandem mass spectroscopy.

Results.

Mammary tissue concentrations of 4-OHT, endoxifen, and telapristone were significantly higher in the axillary glands of the gel-treated animals, compared to inguinal glands or to systemically treated animals. Plasma concentrations were similar in gel and systemically treated animals. The clinical trial showed significantly higher mammary concentrations when diclofenac was applied to the breast skin versus the abdominal skin, but concentrations were variable.

Conclusions.

These results demonstrate that lipophilic drugs can be developed for LTT; although the nude rat is suitable for testing drug permeability, delivery is systemic. In human, however, transdermal application to the breast skin provides local delivery.

Introduction

Despite successful breast cancer prevention trials that established the efficacy of selective estrogen receptor modulators [1] and aromatase inhibitors [2, 3], the acceptance of these drugs by women at high risk of breast cancer has been low. Reasons include quality-of-life impairments, the possibility of more serious side effects, and reluctance by healthy women to take oral medication for prevention. However, breast cancer prevention requires only that the breast be exposed to the drug; systemic exposure is both unnecessary and harmful. Oral tamoxifen is a good example; 5 years of systemic exposure leads to benefits to the breast and bone, but with costs to quality of life and health [4-6]. The avoidance of systemic exposure through prevention strategies that target the breast locally, and have minimal systemic toxicity, may overcome these barriers. One proposed method of local therapy to the breast involves drug delivery to the ductal epithelium by cannulating the ductal orifice with a catheter [7]. However, this requires an office procedure by a specialist, the value of a single injection is not known, the feasibility of multiple injections is untested, and dissemination across multiple practice settings and varied clinical environments seems dubious. A far simpler alternative is transdermal delivery of drugs through the breast skin; its advantages include the avoidance of fast hepatic metabolism, non-invasiveness, and self-administration across the globe without costly devices. Therefore, local transdermal therapy (LTT) to the breast is likely to improve the tolerability and the acceptance of pharmacological cancer prevention regimens by women.

The unique features of the breast predict the success of LTT; these include the embryological origin of the breast as a skin appendage [8] with a well-developed internal lymphatic circulation [9] and the presence of a subcutaneous and retromammary fatty envelope. We hypothesize that the fatty envelope of the breast may serve as drug reservoir for prolonged distribution to the breast, aided by the intramammary lymphatic circulation, so that transdermally delivered drugs are disseminated throughout the breast.

Previous studies of LTT, including our recently completed preoperative trial testing 4-OHT gel in women with ductal carcinoma in situ (DCIS), suggest that delivery is local with minimal systemic exposure and good biological effect [10-12]. These data prompt further questions: (1) Are other drugs candidates for LTT? (2) Is hormone receptor binding required? (3) What is the variability of drug distribution through the breast? In the present report, we describe a series of experiments to address these questions. In a rat model, we compare two tamoxifen metabolites (4-OHT and endoxifen) and test telapristone, an antiprogestational agent. We compare the drug concentrations of mammary tissue and plasma by transdermal delivery, to those achieved by systemic therapy. Given important differences between rodent and human mammary glands, and to test a non-steroid receptor binding drug, we have conducted a clinical trial to test the hypothesis that application of a transdermal diclofenac patch on the breast will result in higher breast concentrations of diclofenac than patch application to the abdomen, thus establishing that LTT to the breast constitutes local rather than systemic therapy.

Materials and Methods

Materials.

(Z) tamoxifen was purchased from Toronto Research Chemicals, Inc. (Toronto, Canada). 4-OHT (E:Z=50:50), oleic acid, sesame oil, and anhydrous ethanol were purchased from Sigma-Aldrich, Inc. (Z) endoxifen citrate salt (>97%) was a gift from Jina Pharmaceuticals, Inc. (Libertyville, Ill., USA). Telapristone was a gift from Repros Therapeutics, Inc. (The Woodlands, Tex., USA). Klucel hydroxypropyl cellulose (viscosity-type HF, 30,000 mPas) was purchased from Hercules Incorporated (Wilmington, Del., USA). Telapristone pellets (30 mg, 60 days release) were manufactured by Innovative Research of America, Inc. (Sarasota, Fla., USA). Customized rat jackets were manufactured by Lomir Biomedical, Inc. (Quebec, Canada). Diclofenac patches (Flector® patches) were purchased from Pfizer Inc.

Preparation of Medications for Rats.

(Z) tamoxifen was prepared as 3 mg/mL in sesame oil. For transdermal gel formulations, 4-OHT (E:Z=50:50) (1 mg/mL), (Z) endoxifen (1 mg/mL), and telapristone (1.5 mg/mL) were prepared in 60% (v/v) ethanol-phosphate buffer containing 0.5% (v/v) oleic acid [13] with 1.5% (w/v) Klucel hydroxypropyl cellulose.

Animal Studies and Treatments.

Figure 2:
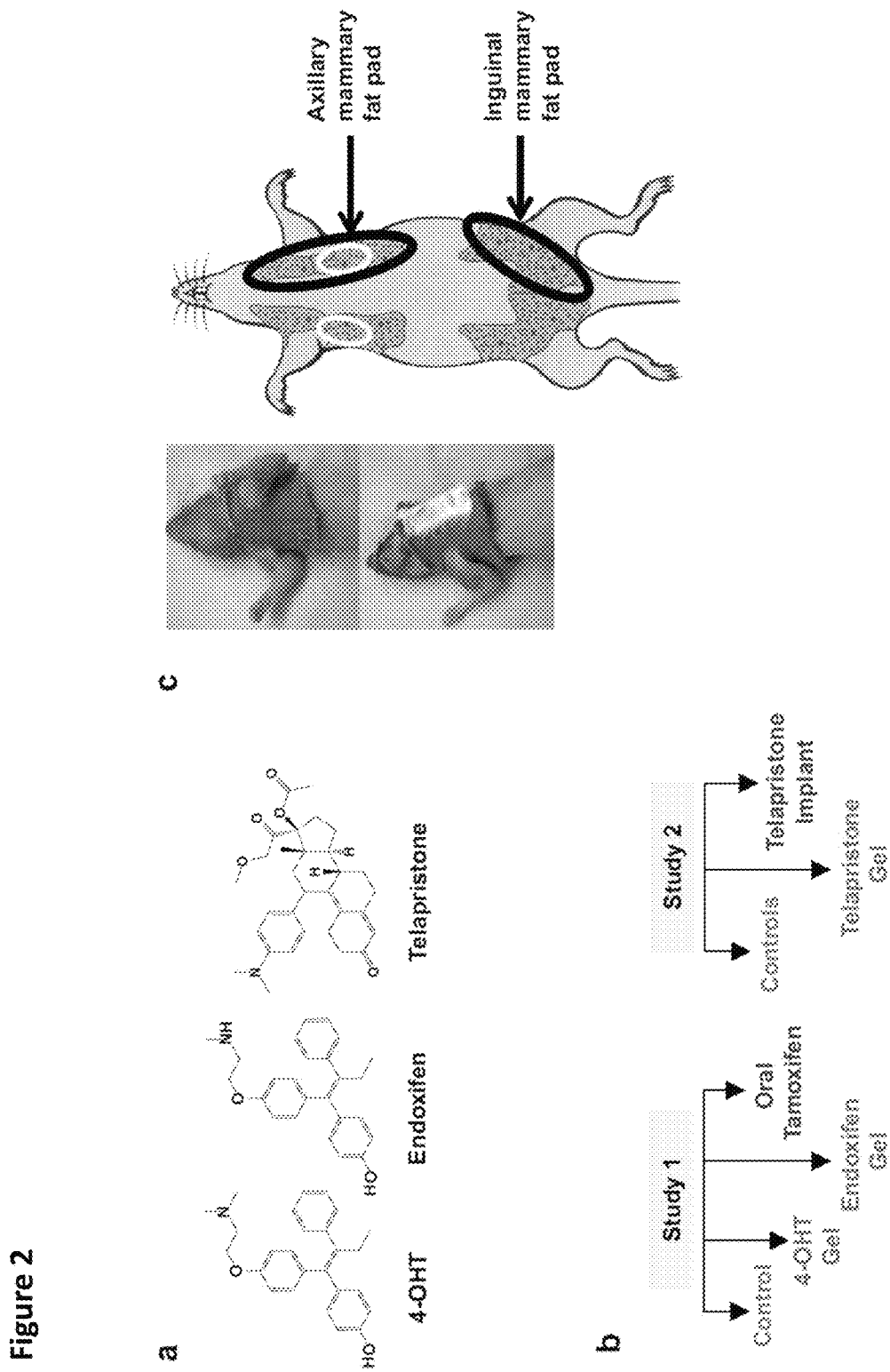
FIG. 2. Preclinical studies to test local transdermal therapy to mammary tissues. a. Chemical structures of study drugs. b. Preclinical studies were designed to compare transdermal delivery with systemic delivery methods. The control group of Study 1 was no treatment group, and the rats treated with placebo pellet and placebo gel were the control groups of Study 2. c. Transdermal gels were applied to the skin area around second nipples of axillary mammary glands, and jackets were used to prevent the drug ingestion by the animals. Axillary and inguinal mammary fat pads and blood from heart were collected for determination of drug concentration FIG. 3. Clinical trial to evaluate the distributions of diclofenac within the breast. a Chemical structure of diclofenac and the study schema. Women waiting for mastectomy were randomized either to breast patch group or to abdominal patch group of diclofenac using Flector Patch®. b Fresh tissues were collected from predetermined sampling locations of the breast (1 through 8): an upper central (1), an outer central (2), a lower central (3), an inner central (4), an upper peripheral (5), an outer peripheral (6), a lower peripheral (7), and an inner peripheral (8) area. UIQ upper inner quadrant, UOQ upper outer quadrant, LIQ lower inner quadrant, LOQ lower outer quadrant. In the breast patch group, the patch (line) was worn over the upper outer breast, with the lower inner corner of the patch at the level of the nipple. Highlighted inner central and peripheral locations (4, 5, 7, and 8) of breast patch group had significantly higher amount of diclofenac compared to abdominal patch group, and an outer peripheral location (6) contained the least amount of diclofenac in breast patch group. c Representative compositions of the breast samples. Note that we sub-categorized tissue samples into three types: fatty type if the tissue on slide contains >75% adipocytes; fibrous type if >75% fibrous stroma; and mixed type (otherwise compositions). Diclofenac concentrations by the tissue compositions were represented in a scatter plot with median values (bars). *p<0.001.

Studies 1 and 2, see FIG. 2: Animal experiments were approved by the Animal Care and Use Committee of Northwestern University. Athymic nude rats (Hsd:RHFoxn1$^{rnu}$/$_{rnu}$, Harlan Laboratories, Inc.) were provided with standard laboratory food and water ad libitum. In Study 1, rats weighting 180-200 g were randomized to four groups (no treatment control, 4-OHT gel, endoxifen gel, and oral tamoxifen) and treated daily for 6 weeks. In the gel groups, animals were anesthetized with isoflurane inhalation; the skin surface of axillary mammary glands was cleaned with alcohol swabs and air-dried; 0.1 mL drug gel was applied using a template with an exposed ellipse ($\pi \times R_1 \times R_2 = \pi \times 1$ cm$\times$0.6 cm) around the no. 2 nipple on each side and allowed to dry (total of 1, 0.5 mg/kg/day on each side); animals wore jackets fitted over the forelegs, to prevent loss of gel through grooming. In the oral tamoxifen group, the tamoxifen (3 mg/kg/day) was delivered through feeding needles (20G-3", Cadence Science Inc.), and the animals wore jackets and were exposed to anesthesia similar to the transdermal treatment group.

In Study 2, we compared subcutaneous versus transdermal administration of telapristone. Rats were randomized to three groups (no treatment control, telapristone gel, and telapristone implant). The transdermal group was prepared and treated with telapristone gel (1.5 mg/kg/day) similar to Study 1. The implant group was subcutaneously given with telapristone pellet (30 mg, 60 days release) in lower dorsal area and delivered 2.5 mg/kg/day, assuming zero-order kinetics. All rats wore jackets and were exposed to anesthesia.

In both studies, rats were euthanized after 6 weeks of treatment for blood and tissue collections. The treated skin area was cleansed with alcohol prior to dissection. Blood samples were collected from the heart. We collected the whole mammary glands (1 axillary and 1 inguinal) per animal and measured their drug concentrations separately.

Study 3: Diclofenac Patch in Women.

A pilot study to test the uniformity of transdermal drug delivery to the breast using diclofenac epolamine patch was approved by the Northwestern University Institutional Review Board (http://www.clinicaltrials.gov, NCT01380353). Nonpregnant women scheduled for mastectomy to prevent or treat breast cancer were recruited through the Lynn Sage Comprehensive Breast Center of Northwestern Medicine. All participants were randomized to patch application to one surgical breast (per participant) or the abdominal skin. The diclofenac patch (Flector® patch, 10 cm×14 cm) is a semi-occlusive, bioadhesive patch containing 129.7 mg of diclofenac acid. After baseline evaluation, the participants were instructed on site of patch application and to replace patch every 12 h over 72 h prior to surgery.

Figure 3:
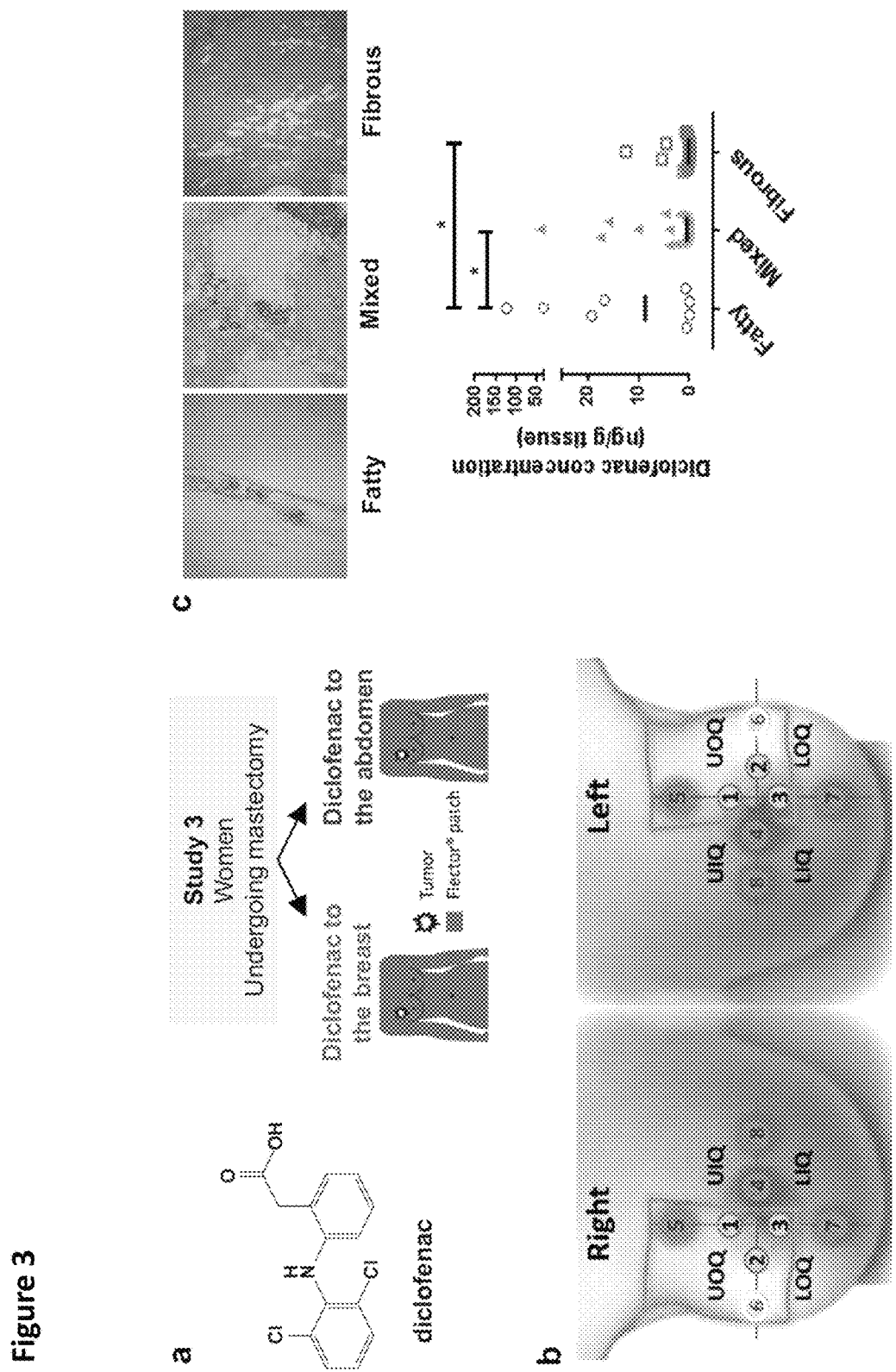

The structure of diclofenac and schema of patch applications are shown in FIG. 3a. The breast group wore the patch over the upper outer breast, with the lower inner corner of the patch at the level of the nipple (FIG. 3b). The abdominal group wore the patch on the lower abdomen on the side opposite the planned mastectomy (FIG. 3a). Participants were assessed for baseline signs/symptoms and then by telephone the second day of the treatment and on the day of surgery. All adverse events were coded using the NCI Common Terminology Criteria for Adverse Events version 4.0.

On the day of surgery, the transdermal patch was removed in the operating room prior to anesthesia and 30 mL venous blood was collected with anticoagulant K2EDTA (BD Vacutainer®, BD Hemogard™ product no. 366643). Tissue samples from the mastectomy specimen were obtained from eight predetermined locations of one breast per participant (FIG. 3b), four central/periareolar and four peripheral samples 5 cm away, at 12, 3, 6, and 9 O'clock. Each tissue sample was weighed and snap-frozen in liquid nitrogen and kept in −80° C. until analysis.

Formalin-fixed, paraffin-embedded (FFPE) samples were taken from locations adjacent to the drug assay samples, for histological evaluation of tissue composition, and were available from all subjects. For the last nine subjects, each frozen tissue sample taken for drug assay had a face shaving taken for the evaluation of tissue composition before freezing.

Quantitation of Plasma and Tissue Concentrations of Drugs.

The concentrations of all the drugs used in rats and humans were determined by liquid chromatography-tandem mass spectroscopy (API 3000; AB SCIEX, Foster City, Calif., USA). Chromatographic separation was achieved with a Kinetex C18 2.6-μm column (50 mm×2.1 mm, Phenomenex, Torrance, Calif., USA) for rat samples and a BETASIL Phenyl-Hexyl 3-μm column (30×2.1 mm, Thermo Fisher Scientific Inc., Waltham, Mass., USA) for human samples. The mobile phase was A: 0.1% formic acid in water (v/v) and B: 0.1% formic acid in acetonitrile (v/v). Details of sample processing and quantitation methods are described below. The lowest limits of quantification (LLOQ) were as follow: tamoxifen and N-desmethyl tamoxifen (NDT) (plasma 10 ng/mL; tissue 40 ng/g); 4-OHT and endoxifen (plasma 0.5 ng/mL; tissue 2 ng/g); telapristone and N-desmethyl telapristone (d-telapristone) (plasma 1 ng/mL; tissue 1.5 ng/g); and diclofenac (plasma 0.5 ng/mL; tissue 2 ng/g).

Statistical Design and Analysis.

For preclinical studies, the summary statistics as medians and interquartile range (IQR) were reported by treatment group for each analyte obtained from plasma, axillary, and inguinal mammary glands. Concentration differences of each analyte between treatment groups and differences between mammary glands within each treatment group were assessed via the Wilcoxon rank-sum test, and the Wilcoxon signed rank-sum test, respectively. In the diclofenac clinical study, categorical variables comparing women in the treatment groups were compared using Fisher's exact test (Table 8). The medians and IQR's were reported for diclofenac concentrations by breast region and patch groups (Table 9). To compare breast concentrations by site of patch application, we replaced non-detectable values with "zero" and considered the median concentration from eight samples as the representative breast concentration per individual for statistical purposes. The Wilcoxon rank-sum test was used to assess median concentration differences between patch groups, among regions of the breast, and by menopausal status within each treatment group.

Method Description of Quantitation Methods by Liquid Chromatography-Tandem Mass Spectroscopy (LCMS/MS).

Study 1:

(Z) tamoxifen and metabolites [(Z) NDT, (E) 4-OHT, and (Z) 4-OHT, (Z) endoxifen] were determined using LC-MS/MS (API 3000; AB SCIEX, Foster City, Calif.). A 100 μL aliquot of plasma was mixed with 200 μL of acetonitrile containing 1 ng each of the deuterated analogs of the analytes (TRC, Toronto, Canada). After vortex-mixing for five minutes, the sample was centrifuged at 4° C. and 7000 RPM for 10 minutes, the supernatant transferred to an autosampler vial and diluted with 200 μL of water before analysis. Rat mammary tissue specimens were finely cut with surgical scalpels and extracted with 0.2 mL of 50% methanol in water (v/v), 2 mL of saline and 4 mL of acetonitrile containing 20 ng of each of the internal standards. The sample tubes were capped and shaken in a mechanical shaker for 2 h. The resulting extract was centrifuged as above and a 300 μL aliquot diluted with 200 μL of water for analysis. Chromatographic separation was achieved with a Kinetex PFP 2.6μ column, 50×2.1 mm (Phenomenex, Torrance, Calif.). The mobile phase was A: 0.1% formic acid in water (v/v) and B: 0.1% formic acid in acetonitrile (v/v). After injection, initial conditions with A at 60% were held for 2 min, decreased to 30% in 4 min and then to 5% (step gradient) for 3 min, returning to initial conditions for 4 min of re-equilibration time. The flow rate was 0.3 ml/min at 25° C. Retention times for (Z) tamoxifen, (Z) NDT, (E) 4-OHT, (Z) 4-OHT and (Z) endoxifen were 8.6, 7.9, 5.2, 5.7 and 5.6 and min, respectively. Total run time was 13 min A turbo ion spray interface was used as the ion source operating in positive mode. Acquisition was performed in multiple reaction monitoring mode using m/z 372.2→72.1, 358.2→58.2, 388.2→72.1 and 374.2→58.2 at low resolution for tamoxifen, NDT, 4-OHT and endoxifen, respectively.

Study 2:

Telapristone, and its main metabolite (d-telapristone) were determined using LC-MS/MS (API 3000; AB SCIEX, Foster City, Calif.). A 100 μL aliquot of rat plasma was mixed with 200 μL of acetonitrile containing 25 ng of the mifepristone (used as internal standard, Sigma-Aldrich, St. Louis, Mo.). After vortex-mixing for one minute, the sample was centrifuged at 4° C. and 7000 RPM for 10 minutes, the supernatant transferred to an autosampler vial and diluted with 400 μL of water before analysis. Rat mammary tissue specimens were finely cut with surgical scalpels and homogenized with acetonitrile using a 1:2 (w/v) ratio. A 200 μL aliquot of the resulting homogenate was extracted with 0.3 mL of water and 1 mL of methyl ter-butyl ether containing 20 ng of mifepristone (RU486). After vortex-mixing for 5 min, the samples were centrifuged to remove precipitated proteins, stored in a freezer at approximately –70° C. for at least an hour, and then the top layer decanted into a clean tube and evaporated under nitrogen flow. The residue was reconstituted in 250 μL of 40% acetonitrile in water, vortex-mixed for ten minutes, and centrifuged again; the resulting supernatant was transferred to an autosampler vial for instrumental analysis. Chromatographic separation was achieved with a Kinetex C18 2.6 μm column, 50 mm×2.1 mm (Phenomenex, Torrance, Calif.). The mobile phase was A: 0.1% formic acid in water (v/v) and B: 0.1% formic acid in acetonitrile (v/v). After injection, initial conditions with A at 70% were held for 0.5 min, decreased to 5% in 2.5 min, held for 3 min at the same conditions and returned to initial conditions in one min for 3 min of re-equilibration time. The flow rate was 0.3 ml/min at 35° C. Retention times for telapristone and d-telapristone were 2.1 and 1.5 min, respectively. Total run time was 10 min A turbo ion spray interface was used as the ion source operating in positive mode. Acquisition was performed in multiple reaction monitoring mode using m/z 506.4→134.3 and 492.2→120.2 at low resolution for telapristone and d-telapristone, respectively.

Study 3:

Diclofenac was determined by LC-MS/MS (API 3000; AB SCIEX, Foster City, Calif.). A 100 μL aliquot of plasma was mixed with 200 μL of acetonitrile containing 5 ng of diclofenac-d4 (internal standard; CDN Isotopes, Quebec, Canada). After vortex-mixing for five minutes, the sample was centrifuged at 4° C. and 7000 RPM for 10 minutes and the supernatant transferred to an autosampler vial for analysis. For breast tissue analysis, approximately 100 mg of material was mixed with 400 μL of saline and 1.5 mL of acetonitrile containing 25 ng of internal standard and shaken for 2 h. The resulting extract was centrifuged as above and an aliquot submitted for analysis. Chromatographic separation was achieved with a BETASIL Phenyl-Hexyl 3 μm column, 30×2.1 mm (Thermo Fisher Scientific Inc., Waltham, Mass.). The mobile phase was A: 0.1% formic acid in water (v/v) and B: 0.1% formic acid in acetonitrile (v/v). After injection, initial conditions with A at 50% were held for 0.5 min, decreased to 5% in 0.5 min and held for 3 min, returning to initial conditions in 0.5 min for 3.5 min of re-equilibration time. The flow rate was 0.3 ml/min at 25° C. Retention time for diclofenac was 1.4. Total run time was 8 min A turbo ion spray interface was used as the ion source operating in positive mode. Acquisition was performed in multiple reaction monitoring mode using m/z 296.0→214.0 and 298.0→216.0.

Results

The structures and the study schema of the agents for LTT studies are summarized in FIG. 2a, b for the preclinical studies, and in FIG. 3a for the clinical study.

Study 1: Oral TAM Versus Transdermal 4-OHT and Endoxifen Delivery in Rats.

We used a mixture of 4-OHT isomers (E:Z=50:50) and the (Z) endoxifen isomer (>97% pure) for transdermal gel formulations since these compounds have been used in human trials of transdermal 4-OHT gel [14] and oral endoxifen [15]. The (Z) isomers of 4-OHT and endoxifen are believed to be highly anti-estrogenic, whereas the (E) isomers are not [16]; both isomers have equivalent binding affinities to ERα [17].

Mammary Concentrations [Table 6(a)].

Oral tamoxifen treatment resulted in mammary concentrations that were highest for NDT followed by tamoxifen, then endoxifen, and 4-OHT. Concentrations were significantly higher in inguinal than in axillary glands ($p^\$=0.02$ for all).

In the 4-OHT gel group, the mammary concentrations of (Z) 4-OHT were fourfold higher at the site of application (the axillary gland) than in the inguinal gland (p$=0.008). The axillary mammary concentration of (Z) 4-OHT was about sevenfold higher in the 4-OHT gel group than in the oral tamoxifen group (25.5 vs. 3.90 g/g, p<0.001), whereas the inguinal concentration was comparable with that of the oral group (6.62 vs. 5.06 ng/g, p=0.49). Furthermore, at both locations, the concentration of (Z) 4-OHT was higher than that of (E) 4-OHT (Z:E=3:1 for the axillary gland, p=0.001; 6:1 for the inguinal gland, p<0.001). There was minimal conversion of 4-OHT to endoxifen in the 4-OHT gel group; the (Z) endoxifen concentration of the 4-OHT gel group was 0.34 and 0.27 ng/g in axillary and inguinal glands, respectively, significantly lower than in the oral tamoxifen group (p<0.001).

In the endoxifen gel group, the concentration of (Z) endoxifen in the axillary gland was over fivefold higher than in the inguinal gland ($p^\$=0.004$), and eightfold higher than in axillary glands of the oral tamoxifen group (p<0.001). The inguinal concentration of (Z) endoxifen was similar to that of the oral tamoxifen group (p=0.43). Comparing the axillary glands of the two gel groups, the (Z) endoxifen concentration of the endoxifen gel group was higher than the (Z) 4-OHT concentration of the 4-OHT gel group (37.3 vs. 25.5 ng/g). Inguinal gland concentrations were similar (7.29 vs. 6.62 ng/g).

Plasma Concentrations [Table 6(b)].

The plasma concentrations of tamoxifen and its metabolites in the oral tamoxifen treatment group were: NDT>tamoxifen>endoxifen>4-OHT. In both gel groups, plasma concentrations were similar to the oral tamoxifen group; (Z) 4-OHT 1.61 versus 2.48 ng/mL, p=0.39 and (Z) endoxifen 1.81 versus 2.96 ng/mL, p=0.77. In the endoxifen gel group, we found trace levels of (Z) 4-OHT in the plasma of the endoxifen group (0.30 ng/mL), far lower than the levels in the oral tamoxifen group (p=0.003) or the 4-OHT gel group (p#=0.002).

Study 2: Comparison of Transdermal Versus Subcutaneous Implant of Telapristone in Rats.

Telapristone is known to be primarily converted by CYP 3A4 in the liver to N-desmethyl telapristone (d-telapristone), a metabolite with similar anti-tumor activity; we measured both forms.

Mammary Concentrations [Table 7(a)].

In the telapristone implant group, the concentration ratio of telapristone to d-telapristone was approximately 6 for both axillary and inguinal glands. The mammary concentrations of both telapristone and d-telapristone were higher in the inguinal gland than in the axillary gland (p$=0.055 for telapristone; $p^\$=0.03$ for d-telapristone). In the telapristone gel group, the mammary concentration of telapristone was sevenfold higher in axillary gland than in the inguinal gland (1212 vs. 167 ng/g, p$<0.004) and 26-fold higher than in the implant group (1212 vs. 46.5 ng/g, p<0.001). The inguinal mammary concentration of telapristone was threefold higher in the gel group than in the implant group (167 vs. 53.1 ng/g, p=0.02). The axillary mammary concentrations of d-telapristone was fourfold higher in the gel group than in the implant group (28.4 vs. 7.21 ng/g, p<0.001), whereas the inguinal mammary concentration of d-telapristone was non-significantly lower in the gel group than in the implant group (6.05 vs. 8.42 ng/g, p=0.09).

TABLE 6

Mammary and plasma concentration of tamoxifen and its metabolites (Study 1)

(a) Mammary concentration (median with IQR, ng/g tissue)

| Analytes | Oral tamoxifen (3 mg/kg/day) | | | 4-OHT gel (1 mg/kg/day) | | | | | Endoxifen gel (1 mg/kg/day) | | | | |
|---|---|---|---|---|---|---|---|---|---|---|---|---|---|
| | Axillary N = 8 | Inguinal N = 8 | p$ | Axillary N = 9 | p | Inguinal N = 9 | p | p$ | Axillary N = 9 | p | Inguinal N = 9 | p | p$ |
| (Z) Tamoxifen | 44.2 (30.2, 51.0) | 69.6 (57.4, 129) | 0.02 | ND | | ND | | | ND | | ND | | |
| (Z) NDT | 51.0 (44.7, 65.6) | 107 (64.9, 168) | 0.02 | ND | | ND | | | ND | | ND | | |
| (E) 4-OHT | ND | ND | | 7.28 (3.62, 9.91) | | 1.09 (0.79, 1.64) | | 0.004 | ND | | ND | | |
| (Z) 4-OHT | 3.90 (2.14, 4.98) | 5.06 (3.18, 10.0) | 0.02 | 25.5 (19.2, 48.7) | <0.001 | 6.62 (5.44, 10.4) | 0.49 | 0.008 | 0.24 (0.00, 0.40) | <0.001 | 0.12 (0.00, 0.19) | | 0.11 |
| (Z) Endoxifen | 4.46 (2.76, 6.30) | 5.87 (4.34, 12.4) | 0.02 | 0.34 (0.25, 0.62) | <0.001 | 0.27 (0.21, 0.35) | <0.001 | 0.73 | 37.3 (31.1, 60.3) | <0.001 | 7.29 (6.88, 16.3) | 0.43 | 0.004 |

(b) Plasma concentration (median with IQR, ng/mL)

| Analytes | Oral tamoxifen N = 8 | 4-OHT gel N = 9 | p | p* | Endoxifen gel N = 9 | p | p# |
|---|---|---|---|---|---|---|---|
| (Z) Tamoxifen | 8.00 (7.17, 10.4) | ND | | | ND | | |
| (Z) NDT | 12.1 (9.78, 16.4) | ND | | | ND | | |
| (E) 4-OHT | ND | 0.14 (0.10, 0.18) | | | ND | | |
| (Z) 4-OHT | 2.48 (1.32, 2.95) | 1.61 (1.30, 2.09) | 0.39 | <0.001 | 0.30 (0.00, 0.48) | 0.003 | 0.002 |
| (Z) Endoxifen | 2.96 (1.50, 3.48) | ND | | | 1.81 (1.25, 17.2) | 0.773 | |

Comparisons by the Wilcoxon rank-sum test were p = each treatment group with the oral tamoxifen group, p* = between two isomers of 4-OHT in the 4-OHT gel group, p# = 4-OHT gel group versus ENX gel group, and by the Wilcoxon signed rank test were p$ = between two glands within each treatment group
IQR interquartile range,
ND not detectable

TABLE 7

Mammary and plasma concentration of tamoxifen and its metabolites (Study 2)

(a) Mammary concentration (median with IQR, ng/g tissue)

| | Telapristone implant (2.5 mg/kg/day) N = 9 | | | Telapristone gel (1.5 mg/kg/day) N = 9 | | | | |
|---|---|---|---|---|---|---|---|---|
| Analytes | Axillary N = 9 | Inguinal N = 9 | p$ | Axillary N = 9 | p | Inguinal N = 9 | p | p$ |
| Telapristone | 46.5 (33.4, 56.8) | 53.1 (44.3, 55.6) | 0.055 | 1212 (962, 1701) | <0.001 | 167 (107, 270) | 0.02 | 0.004 |
| D-Telapristone | 7.21 (5.07, 10.1) | 8.42 (6.78, 10.0) | 0.03 | 28.4 (24.9, 31.8) | <0.001 | 6.05 (2.56, 7.95) | 0.09 | 0.004 |

(b) Plasma concentration (median with IQR, ng/mL)

| Analytes | Telapristone implant N = 9 | Telapristone gel N = 9 | p |
|---|---|---|---|
| Telapristone | 13.2 (12.0, 13.3) | 10.9 (7.47, 13.7) | 0.12 |
| D-Telapristone | 3.99 (3.70, 4.44) | 1.33 (1.18, 1.75) | <0.001 |

Comparisons by the Wilcoxon rank-sum test were p = between two treatment group, and by the Wilcoxon signed rank test were p$ = between two glands within each treatment group Plasma Concentrations [Table 7(b)].

The plasma concentration of telapristone in the gel group (dose 1.5 mg/kg/day) was similar to the level of the implant group (10.9 vs. 13.2 ng/mL, p=0.12). However, plasma concentrations of d-telapristone were significantly lower in the gel group than in the implant group (1.33 vs. 3.99 ng/mL, p<0.001).

Study 3: A Clinical Trial of Transdermal Diclofenac to the Breast or to the Abdomen.

Thirty women planning mastectomy were enrolled (September 2011-November 2012) and randomized to the breast group or the abdominal group. The diclofenac patch application started 3 days prior to surgery. Two women were withdrawn from analysis due to incorrect use of patch, and one withdrew consent, leaving 27 evaluable women: 14 in the abdominal and 13 in the breast group. The participant characteristics were similar between groups (Table 8).

Breast Concentrations [Table 9(a)].

We measured diclofenac concentrations using fresh-frozen tissue samples collected from eight predetermined locations of the mastectomy specimen (FIG. 3b). In the abdominal group, 65/112 tissue samples (58%) demonstrated detectable diclofenac. Two women had no detectable diclofenac, nine displayed trace levels, and three showed a range of concentrations (1.2-4.8 ng/g) in their tissue samples. In the breast group, diclofenac concentrations were measured in 96 (of 104 expected) tissue samples because we were not able to obtain all eight samples from two women. Diclofenac was detectable in all 13 women in the breast group and in 79% (76/96) of tissue samples, although three women showed trace levels. A large variation in diclofenac breast tissue concentrations was observed, both within and between subjects. The overall breast concentration of diclofenac of the breast group was sixfold higher than that of the abdominal group (0.77 vs. 0.13 ng/g, p=0.02).

The variation in diclofenac distribution throughout the breast was greater in the breast than in the abdominal group. Within each group, diclofenac concentrations were similar between the central locations (1 through 4) and peripheral locations (5 through 8). In the abdominal group, the median concentrations were 0.85 ng/g centrally versus 0.75 ng/g peripherally (p=0.42); in the breast group, they were 4.91 ng/g centrally versus 9.92 ng/g, peripherally (p=0.78). In both central and peripheral locations, the breast group had significantly higher median concentrations than the abdominal group (p=0.006 for central and p<0.001 for peripheral locations). The outer peripheral location (location 6, FIG. 3b) contained the lowest amount of diclofenac in breast group [Table 9(a)], but even here the concentration remained higher in the breast patch than in the abdominal patch group (0.31 vs. 0.04 ng/g tissue).

TABLE 8

Baseline clinical characteristics according to patch groups (Study 3)

| The site of patch application | Abdomen (N = 14) | Breast (N = 13) | P |
|---|---|---|---|
| Age, years (median with IQR) | 47 (43, 54) | 46 (39, 57) | 0.87 |
| Menopausal status | | | |
| Pre | 8 (57.1%) | 7 (53.8%) | 0.99 |
| Post | 6 (42.9%) | 6 (46.2%) | |
| Race | | | |
| Caucasian | 13 (92.9%) | 10 (76.9%) | 0.33 |
| Non-Caucasian | 1 (7.1%) | 3 (23.1%) | |
| Indication for mastectomy | | | |
| BRCA2 mutation | 3 (21.4%) | 3 (23.0%) | 0.78 |
| High risk (family history, ADH/ALH) | 1 (7.10%) | 2 (15.4%) | |
| DCIS | 0 (0.00%) | 1 (7.70%) | |
| IDC/ILC | 10 (71.4%) | 7 (53.9%) | |
| Breast size (bra cup sizes) | | | |
| Small (A/B) | 5 (35.7%) | 6 (46.2%) | 0.99 |
| Medium (C/D) | 7 (50.0%) | 6 (46.2%) | |
| Large (DD/E/H) | 2 (14.3%) | 1 (7.70%) | |
| Body mass index (BMI) | | | |
| Median with IQR | 24.9 (23.8, 32.9) | 24.8 (22.9, 34.7) | 0.96 |
| Normal (BMI 18.5-24.9) | 7 (53.9%) | 7 (53.9%) | |
| Overweight (BMI 25-29.9) | 2 (14.3%) | 0 (0.00%) | |
| Obese (BMI 30 or greater) | 5 (35.7%) | 6 (46.2%) | |
| Tissue feature of breast specimen | | | |
| Fatty | 0 (0.00%) | 3 (23.1%) | 0.10 |
| Otherwise | 14 (58.3%) | 10 (76.9%) | | p values (comparisons between two treatment groups) were calculated with the Wilcoxon rank-sum test for continuous variables and with the Fisher's exact test for categorical variables

TABLE 9

Breast and plasma concentrations of diclofenac (Study 3)

(a) Breast concentration (median with IQR, ng/g tissue)

| Sampling locations | Abdominal patch | (N = 112) | Breast patch | (N = 96) | P |
|---|---|---|---|---|---|
| 1 | 0.00 (0.00, 0.37) | (N = 14) | 0.63 (0.00, 8.23) | (N = 12) | 0.15 |
| 2 | 0.18 (0.00, 0.87) | (N = 14) | 0.64 (0.17, 5.42) | (N = 11) | 0.20 |
| 3 | 0.20 (0.00, 0.48) | (N = 14) | 0.48 (0.00, 2.71) | (N = 13) | 0.30 |
| 4 | 0.19 (0.00, 0.72) | (N = 14) | 1.64 (0.35, 13.1) | (N = 12) | 0.007 |
| 5 | 0.11 (0.00, 0.36) | (N = 14) | 1.98 (0.67, 13.7) | (N = 12) | 0.003 |
| 6 | 0.04 (0.00, 0.48) | (N = 14) | 0.31 (0.00, 1.23) | (N = 11) | 0.28 |
| 7 | 0.14 (0.00, 0.37) | (N = 14) | 1.12 (0.30, 3.96) | (N = 12) | 0.01 |
| 8 | 0.08 (0.00, 0.28) | (N = 14) | 0.58 (0.36, 1.37) | (N = 13) | 0.02 |
| All locations | 0.13 (0.00, 0.37) | | 0.77 (0.23, 2.97) | | 0.02 |

(b) Plasma concentration (median with IQR, ng/mL)

| Abdominal patch (N = 14) | Breast patch (N = 13) | P |
|---|---|---|
| 1.06 (0.81, 1.88) | 1.02 (0.71, 1.78) | 0.73 |

N = the number of samples for the measurements,
p values (comparisons between two treatment groups) were calculated with the Wilcoxon rank-sum test Drug Concentrations by Tissue Composition of the Breast Samples.

Based on histological examination of FFPE and frozen samples for drug quantitation (see "Materials and methods"), we categorized tissue samples into fatty, fibrous, and mixed types (FIG. 3c). The proportion of fatty, fibrous, and mixed samples was similar between the 134 FFPE and the 72 frozen samples. For both FFPE and frozen sample, the mixed-type samples were most numerous (58-62%), followed by the fibrous (20-30%) and then the fatty type (11-18%) (FIG. 2a). Among the 72 frozen samples from nine women, the distribution in the abdominal group was: two fatty, 10 fibrous, and 20 mixed samples; in the breast group, six fatty, 12 fibrous, and 22 mixed samples. Since there were only eight fatty samples, we did not separate the samples by patch group for the analysis. The median breast concentrations of diclofenac with IQR were 8.71 (0.15, 29.4) ng/g in fatty samples, 0.52 (0.13, 1.42) ng/g in the mixed samples, and 0.19 (0.00, 0.58) ng/g in fibrous samples (FIG. 3c). Fatty samples contained significantly more diclofenac than fibrous or mixed type (fatty vs. fibrous, p=0.008; fatty vs. mixed, p=0.005); however, there was no concentration difference between fibrous and mixed tissue types (p=0.93).

Correlations of Diclofenac Breast Concentrations with Age, Body Mass Index (BMI), and Breast Size.

Diclofenac breast concentrations significantly decreased with increasing age in the abdominal group (Spearman correlation coefficient, r=−0.77, p=0.001), but not in the breast group (r=0.20, p=0.51) (FIG. 2b). There was no significant correlation between breast concentration of diclofenac and BMI in either group (r=−0.26, p=0.37 in abdominal group; r=−0.38, p=0.20 in breast group) (FIG. 2c). Finally, to see whether breast size affects drug distribution, we grouped women into small, medium, and large breasts based on bra cup sizes (small=A and B; medium=C and D; large=DD, E, and H). There were 11 women with small, 13 women with medium, and 3 women with large breasts, only one of whom belonged to the breast patch group. We were therefore not able to examine the effect of breast size larger than D cup. There was no significant difference in diclofenac concentration by small or medium breast size within each patch group. In the abdominal group, the median concentrations were 0.60 (0.06, 1.20) ng/g and 0.21 (0.00, 0.32) ng/g for small (n=5)-, and medium-sized breasts (n=7), respectively (p=0.22). In the breast group, corresponding values were 1.12 (0.23, 8.70) ng/g and 1.31 (0.06, 2.97) ng/g for small (n=6)-, and medium-sized (n=6) breasts, respectively (p=0.75).

Plasma Concentrations [Table 9(a)].

The median plasma concentration of diclofenac in the breast patch group was similar to that of the abdominal patch group (1.02 vs. 1.06 ng/mL, p=0.73).

Adverse Events.

We did not observe any skin irritation in rats, changes in general health, or weight loss, among controls, or any of the treatment groups. Women did not report any common side effects including skin irritation due to patch application.

Discussion

There are presently two seminal problems in the field of breast cancer prevention: the low acceptance of proven drugs and the lack of drugs that prevent non-luminal breast cancer. The approach we present here has the potential to address both of these barriers. Since only the breast needs to be exposed to a drug for breast cancer prevention and for therapy of DCIS, effective drug therapy that can be limited to the breast should increase acceptance by reducing toxicity through low systemic exposure. This in turn will allow the development of drugs that will target other sub-types of breast cancer but cannot at present be considered for breast cancer prevention because of safety concerns. Together, these two attributes of local therapy for breast cancer prevention carry the seeds of high-impact innovations in this area.

In the present report, building on encouraging data on LTT with 4-OHT [11, 12], we address key questions that will guide the design of additional trials. In preclinical studies, we assessed whether the nude rat was a suitable model for the study of LTT and evaluated additional drug candidates for LTT. We found that dermal permeation of all three steroid receptor modulators (4-OHT, endoxifen, and telapristone) was excellent, with the highest drug concentrations observed in the targeted axillary mammary gland; markedly lower inguinal gland concentrations were seen in all three transdermal groups. Contrary to expectations, however, plasma levels of these drugs were similar with transdermal and with systemic delivery; thus, the rat model, although useful to define permeability, does not test local therapy. The differences between human and rodent mammary gland topology are important to remember in interpreting these differences, since human data from previous studies [10-12] and the present Study 3 consistently demonstrate the validity of LTT in humans. Using a diclofenac patch, we were able to show that local transdermal delivery provides high concentrations in the breast, compared to transdermal application elsewhere. For the clinical trial, we could not use the same drugs as in the rat studies since these are not currently available for human use, but the use of diclofenac allows us to conclude that selective retention in the breast also occurs with nonsteroidal drugs.

Nevertheless, our rodents studies did demonstrate that excellent axillary mammary concentrations of (Z) 4-OHT, (Z) endoxifen, and telapristone can be achieved by transdermal administration and that this is not dependent on the presence of estrogen receptor-rich tumors, as suggested by previous authors [10, 11]. The high drug concentrations observed in the axillary mammary gland replicate the human data and provide evidence that both of the new drugs tested (endoxifen and telapristone) show superior permeation and retention in the axillary gland, compared to 4-OHT, and are candidates for further development as transdermal agents for the breast.

The plasma concentrations of tamoxifen and its metabolites (NDT, 4-OHT and endoxifen) after oral dosing (3 mg/kg/day) were similar to those observed in previous study comparing rats and humans [18]. Likely reasons for the systemic exposure that we observed with transdermal delivery include the difficulty of ensuring that the gel was applied only to the skin area of the mammary gland/fat pad, given the small area and the flat structure of rat mammary gland/fat pad. Furthermore, rat skin is more permeable than human skin [19, 20], and it is possible that the transdermal doses that we chose were too high. Unfortunately, there is no animal model which perfectly mimics the morphology and physiology of human breast. We used nude rats because they are preferable to mice for the testing of transdermal delivery; rabbits and guinea pigs have been used in dermatotoxicology testing, and the domestic pig is the closest match to human skin. However, the human breast is a three-dimensional structure, each breast has a fatty envelope, is a compact unit with abundant fat and stroma, and a fairly distinct border to the skin envelope. No other nonprimate mammal has a similar anatomy. For these reasons, we conclude that although non-human models can be used to test drug permeability, testing of the local component of the LTT concept needs to be performed in humans.

Surprisingly, for both tamoxifen and telapristone, systemic delivery resulted in higher concentrations of each drug and its metabolites in the inguinal than in the axillary gland. This unequal distribution across mammary glands implies that even with systemic delivery, tissue distribution of drugs in the same organ depends on local conditions.

We cannot comment on the efficacy of transdermal delivery based on the present data, but the effectiveness of endoxifen as a prevention agent is not in question given the long experience with tamoxifen and the emerging data on oral endoxifen [21]. Preclinical data on telapristone are promising [22, 23], but it is untested as a prevention agent in humans. We are presently conducting a presurgical window trial in Stage I-II breast cancer patients, the results of which will guide further development (NCT01800422).

We have previously discussed the importance of the embryological origin of the breast as a modified sweat or eccrine gland [12, 13], with the parenchyma and its skin envelope comprising a single unit with a well-developed internal lymphatic and venous circulation [8, 24, 25]. This anatomy predicts that drugs applied to the breast skin should concentrate in the parenchyma to a greater degree than if applied to skin elsewhere, that LTT can be generalized to any drug that can penetrate the skin, and that receptor binding is not involved. Diclofenac, non-steroidal anti-inflammatory drug (NSAID), is a cyclooxygenase inhibitor and therefore a potentially effective breast cancer prevention agent [26]; it is available as a patch for analgesic use, with low systemic exposure [27]; a tissue reservoir forms when diclofenac is applied to the skin of joints [27, 28]; and binding of diclofenac within the breast to its target enzyme is expected to represent a minor component of its retention in adipose tissue of the breast. Additionally, the absence of cardiovascular and gastrointestinal toxicity or a platelet effect allowed use in the preoperative period. Our clinical trial tested breast application (local) with abdominal application (systemic) of the patch. An additional oral diclofenac group, although ideal, was not feasible related to concerns about platelet effects during the surgical procedure. Our results, showing significantly (sixfold) higher breast tissue concentrations of diclofenac when the patch was applied to the breast, provide proof-of-principle that extends the concept of LTT to non-steroidal drugs.

Transdermal penetration of NSAIDs has been previously reported as variable [28] with high inter-individual variation in plasma and urine levels of exposed subjects. As hypothesized, the breast concentrations of diclofenac of the breast patch group were significantly higher than those of the abdominal patch group, and not surprisingly, plasma concentrations of diclofenac were similar between breast and abdominal patch groups. Diclofenac breast concentrations declined significantly with increasing age in the abdominal patch group, but not in the breast patch group. BMI showed no significant correlation with breast concentration of diclofenac in both groups, and there was a nonsignificant decline in diclofenac concentrations in C-D cup compared to A-B cup-sized breasts.

We found that the tissue distribution of diclofenac in the eight breast regions of each woman was non-homogeneous in both groups, with greater variation in the breast group, where concentrations were also significantly higher. Fatty tissue samples contained significantly more diclofenac than other types, although the small number of fatty samples limits definitive conclusions. Recognizing the complex structure of breast tissue, we used the entire 100-mg tissue specimen for extraction and analyzed drug concentrations in duplicate, but assay variation related to tissue composition remains a concern. It is intriguing that the paucity of drug at location 6 (outer peripheral) in breast group was unlikely due to a mechanical reason (such as patch nonadherence at the edge). Whether this is related to lymphatic circulation, tissue composition, or other factors will need further study, but is reminiscent of the lower drug levels in the axillary gland of rats that were observed with both tamoxifen and telapristone delivered systemically. Of note, there are no previous studies of drug distribution through the breast, even with oral delivery, no gold standard exists, and the degree of variation with oral delivery is unknown. Although breast drug concentrations achieved with transdermal delivery may be lower or more variable than those achieved with oral delivery, it is helpful to recall that for disease prevention drug dose should be defined as the lowest effective dose, rather than the maximal tolerated dose. Along these lines, data on low dose tamoxifen [29] are encouraging and remind us that the more relevant endpoint in early trials of transdermal therapy is biological effect rather than drug concentration.

Our future plans include an assessment of intra-mammary distribution of telapristone following transdermal versus oral delivery and the development of a gel formulation of endoxifen in partnership with the National Cancer Institute, an important consideration since new supplies of 4-OHT gel are not available. Encouragingly, transdermal permeation of both these drugs is superior to that of 4-OHT in the present study, and we have previously reported on the suitability of endoxifen for LTT [13, 30]. Since diclofenac is also available as a gel, this is another potentially fruitful avenue. We are presently conducting focus group studies of high-risk women to assess preferences between drug delivery routes. We continue to work on standardizing methods of drug concentration measurement in breast tissue.

In summary, we found that all three drugs tested in a rat model demonstrated excellent skin permeation with high tissue levels achieved in the target mammary gland; plasma concentrations, however, were similar between transdermal and systemic treatment, likely related to constraints which apply to the rat model. We also found that a diclofenac patch applied to the breasts of women results in significantly higher breast tissue concentrations overall, but with considerable variability across breast regions. Important next questions include definition of the biologically effective dose of transdermally applied drugs and how much variation in drug concentration is compatible with efficacy, recognizing the difficulties in drug concentration measurement in complex tissues.

REFERENCES

1. Cuzick J, Sestak I, Bonanni B, Costantino J P, Cummings S, Decensi A, Dowsett M, Forbes J F, Ford L, LaCroix A Z et al (2013) Selective oestrogen receptor modulators in prevention of breast cancer: an updated meta-analysis of individual participant data. Lancet 381(9880):1827-1834
2. Goss P E, Ingle J N, Ales-Martinez J E, Cheung A M, Chlebowski R T, Wactawski-Wende J, McTiernan A, Robbins J, Johnson K C, Martin L W et al (2011) Exemestane for breast-cancer prevention in postmenopausal women. N Engl J Med 364(25):2381-2391
3. Cuzick J, Sestak I, Forbes J F, Dowsett M, Knox J, Cawthorn S, Saunders C, Roche N, Mansel R E, von M G et al (2013) Anastrozole for prevention of breast cancer in high-risk postmenopausal women (IBIS-II): an international, double-blind, randomized placebo-controlled trial. Lancet 383(9922):1040
4. Fisher B, Costantino J P, Wickerham D L, Redmond C K, Kavanah M, Cronin W M, Vogel V, Robidoux A, Dimitrov N, Atkins J et al (1998) Tamoxifen for prevention of breast cancer: report of the National Surgical Adjuvant Breast and Bowel Project P-1 Study. J Natl Cancer Inst 90(18):1371-1388
5. Port E R, Montgomery L L, Heerdt A S, Borgen P I (2001) Patient reluctance toward tamoxifen use for breast cancer primary prevention. Ann Surg Oncol 8(7):580-585
6. Day R, Ganz P A, Costantino J P, Cronin W M, Wickerham D L, Fisher B (1999) Health-related quality of life and tamoxifen in breast cancer prevention: a report from the National Surgical Adjuvant Breast and Bowel Project P-1 Study. J Clin Oncol 17(9):2659-2669
7. Stearns V, Mori T, Jacobs L K, Khouri N F, Gabrielson E, Yoshida T, Kominsky S L, Huso D L, Jeter S, Powers P et al (2011) Preclinical and clinical evaluation of intraductally administered agents in early breast cancer. Sci Transl Med 3(106):106ra108
8. Ackerman A B, Kessler G, Gyorfi T, Tsou H C, Gottlieb G J (2007) Contrary view: the breast is not an organ per se, but a distinctive region of skin and subcutaneous tissue. Am J Dermatopathol 29(2):211-218
9. Suami H, Pan W R, Mann G B, Taylor G I (2008) The lymphatic anatomy of the breast and its implications for sentinel lymph node biopsy: a human cadaver study. Ann Surg Oncol 15(3):863-871
10. Pujol H, Girault J, Rouanet P, Fournier S, Grenier J, Simony J, Fourtillan J B, Pujol J L (1995) Phase I study of percutaneous 4-hydroxy-tamoxifen with analyses of 4-hydroxy-tamoxifen concentrations in breast cancer and normal breast tissue. Cancer Chemother Pharmacol 36(6):493-498
11. Rouanet P, Linares-Cruz G, Dravet F, Poujol S, Gourgou S, Simony-Lafontaine J, Grenier J, Kramar A, Girault J, Le Nestour E et al (2005) Neoadjuvant percutaneous 4-hydroxytamoxifen decreases breast tumoral cell proliferation: a prospective controlled randomized study comparing three doses of 4-hydroxytamoxifen gel to oral tamoxifen. J Clin Oncol 23(13):2980-2987
12. Lee O, Page K, Ivancic D, Helenowski I, Parini V, Sullivan M E, Margenthaler J A, Chatterton R T Jr, Jovanovic B, Dunn B K et al (2014) A randomized phase II presurgical trial of transdermal 4-hydroxytamoxifen gel versus oral tamoxifen in women with ductal carcinoma in situ of the breast. Clin Cancer Res 20(14):3672-3682
13. Lee O, Ivancic D, Chatterton R T, Rademaker A, Khan S A (2011) In vitro human skin permeation of endoxifen: potential for local transdermal therapy for primary prevention and carcinoma in situ of the breast. Breast Cancer Targets Ther 3(1):61-70
14. Mansel R, Goyal A, Nestour E L, Masini-Eteve V, O'Connell K (2007) A phase II trial of Afimoxifene (4-hydroxytamoxifen gel) for cyclical mastalgia in premenopausal women. Breast Cancer Res Treat 106(3):389-397
15. Ahmad A, Shahabuddin S, Sheikh S, Kale P, Krishnappa M, Rane R C, Ahmad I (2010) Endoxifen, a new cornerstone of breast cancer therapy: demonstration of safety, tolerability, and systemic bioavailability in healthy human subjects. Clin Pharmacol Ther 88(6):814-817
16. Lim Y C, Li L, Desta Z, Zhao Q, Rae J M, Flockhart D A, Skaar T C (2006) Endoxifen, a secondary metabolite of tamoxifen, and 4-OH-tamoxifen induce similar changes in global gene expression patterns in MCF-7 breast cancer cells. J Pharmacol Exp Ther 318(2):503-512
17. Lim Y C, Desta Z, Flockhart D A, Skaar T C (2005) Endoxifen (4-hydroxy-N-desmethyl-tamoxifen) has anti-estrogenic effects in breast cancer cells with potency similar to 4-hydroxy-tamoxifen. Cancer Chemother Pharmacol 55(5):471-478
18. Robinson S P, Langan-Fahey S M, Johnson D A, Jordan V C (1991) Metabolites, pharmacodynamics, and pharmacokinetics of tamoxifen in rats and mice compared to the breast cancer patient. Drug Metab Dispos 19(1):36-43
19. Morimoto Y, Hatanaka T, Sugibayashi K, Omiya H (1992) Prediction of skin permeability of drugs: comparison of human and hairless rat skin. J Pharm Pharmacol 44(8):634-639
20. Bartek M J, LaBudde J A, Maibach H I (1972) Skin permeability in vivo: comparison in rat, rabbit, pig and man. J Invest Dermatol 58(3):114-123
21. Goetz M P, Suman V A, Reid J R, Northfelt D W, Mahr M A, Dockter T, Haluska P J, Kuffel M, Burhow S, Safgren S et al (2013) A first-in-human phase I study of the tamoxifen (TAM) metabolite, Z-endoxifen hydrochloride (Z-Endx) in women with aromatase inhibitor (AI) refractory metastatic breast cancer (MBC) (NCT01327781). The 2013 San Antonio Breast Cancer Symposium 2013
22. Wiehle R D, Christov K, Mehta R (2007) Anti-progestins suppress the growth of established tumors induced by 7,12-dimethylbenz(a) anthracene: comparison between RU486 and a new 21-substituted-19-nor-progestin. Oncol Rep 18(1):167-174
23. Wiehle R, Lantvit D, Yamada T, Christov K (2011) CDB-4124, a progesterone receptor modulator, inhibits mammary carcinogenesis by suppressing cell proliferation and inducing apoptosis. Cancer Prev Res (Phila) 4(3):414-424
24. Povoski S P, Olsen J O, Young D C, Clarke J, Burak W E, Walker M J, Carson W E, Yee L D, Agnese D M, Farrar W B (2006) Prospective Randomized trial comparing intradermal, intraparenchymal, and subareolar injection routes for sentinel lymph node mapping and biopsy in breast cancer. Ann Surg Oncol 13(2):10-11
25. Klimberg V S, Rubio I T, Henry R, Cowan C, Colvert M, Korourian S (1999) Subareolar versus peritumoral injection for location of the sentinel lymph node. Ann Surg 229(6):860-864
26. Cuzick J, Otto F, Baron J A, Brown P H, Burn J, Greenwald P, Jankowski J, La V C, Meyskens F, Senn H J et al (2009) Aspirin and non-steroidal anti-inflammatory drugs for cancer prevention: an international consensus statement. Lancet Oncol 10(5):501-507
27. McCarberg B H, Argoff C E (2010) Topical diclofenac epolamine patch 1.3% for treatment of acute pain caused by soft tissue injury. Int J Clin Pract 64(11):1546-1553
28. Dehghanyar P, Mayer B X, Namiranian K, Mascher H, Muller M, Brunner M (2004) Topical skin penetration of diclofenac after single- and multiple-dose application. Int J Clin Pharmacol Ther 42(7):353-359
29. Decensi A, Robertson C, Viale G, Pigatto F, Johansson H, Kisanga E R, Veronesi P, Torrisi R, Cazzaniga M, Mora S et al (2003) A randomized trial of low-dose tamoxifen on breast cancer proliferation and blood estrogenic biomarkers. J Natl Cancer Inst 95(11):779-790
30. Yang Y, Pearson R M, Lee O, Lee C W, Chatterton R T, Khan S A, Hong S (2014) Dendron-based micelles for topical delivery of endoxifen: a potential chemo-preventive medicine for breast cancer. Adv Funct Mater 24(17): 2442-2449

Example 3. In Vivo Permeation Comparison of Endoxifen-OA Gel with Dendronmicelle Gel Loading with Endoxifen (DM) in Hairless Mice (Cr1:SKH1-Hrhr)

Figure 4:
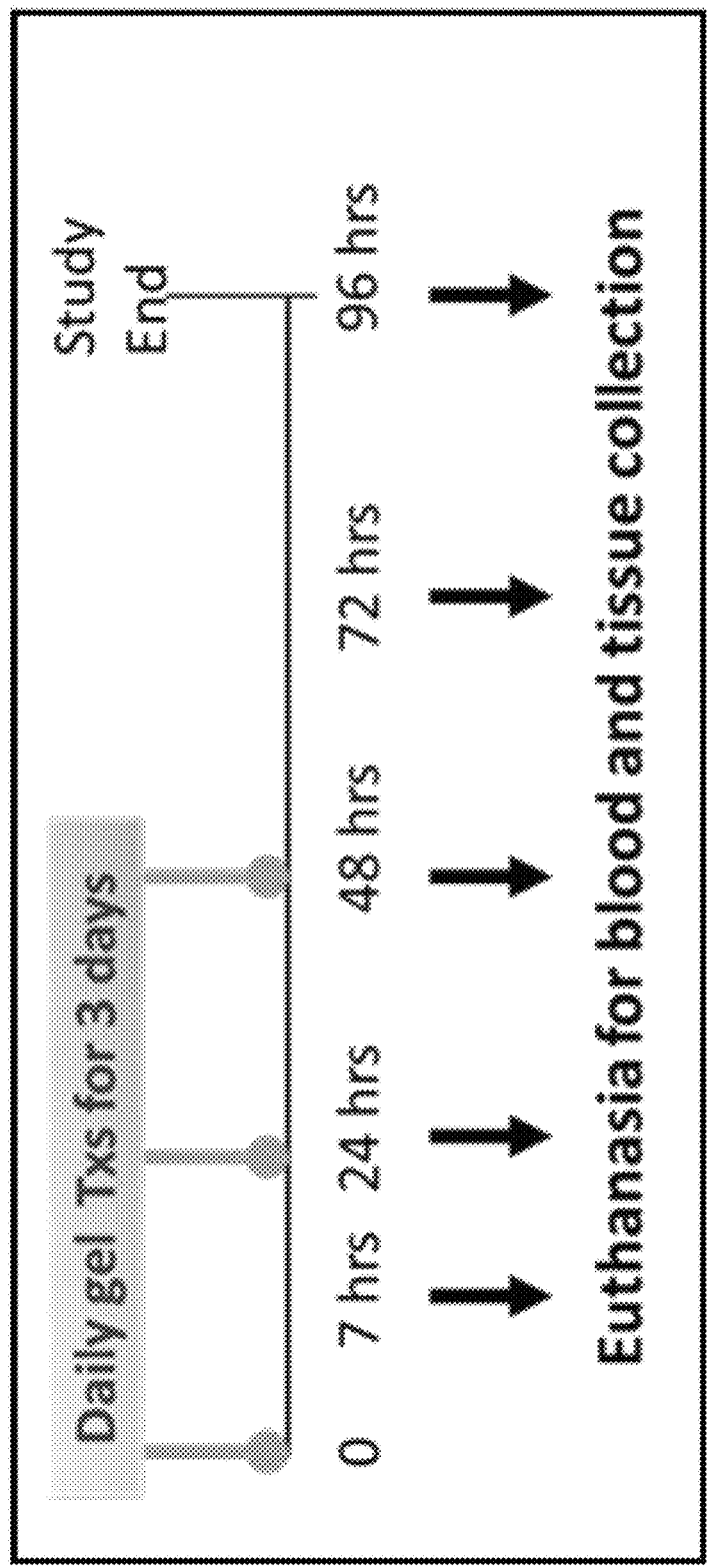
FIG. 4. Study Schema for in vivo skin deposition and plasma concentration of ENX after topical gel treatments under light occlusive conditions.
Figure 5:
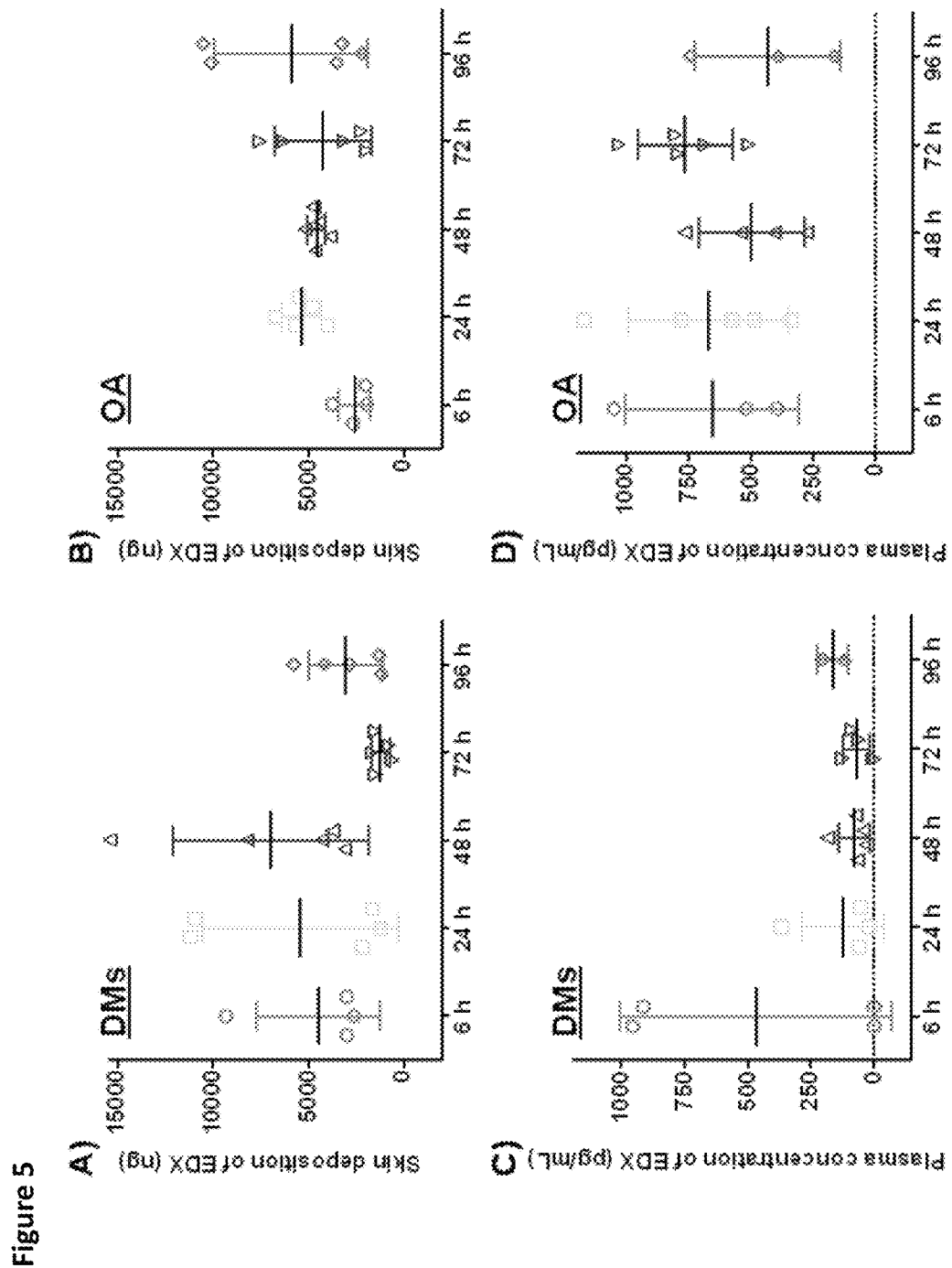
FIG. 5. In vivo skin deposition and plasma concentration of ENX after topical gel treatments under light occlusive conditions (Tegaderm with guaze pad in the middle). In vivo transdermal delivery of ENX-Micelle (DM) vs. ENX-OA gels was compared. Study scheme was presented in top panel. 50 µL of each ENX gel formulation (dose 0.1 mg ENX/day) was applied to upper dorsal skin area and covered with Tegaderm® to prevent gel exposure to animal other than the gel-applied skin area. Daily dose and application volume was 0.1 mg (Z)-endoxifen and 0.05 mL of the gel formulations. ENX-loaded DMs in Klucel gel (indicated as DMs) or free ENX dispersed in Klucel gel containing 0.5% OA and 60% ethanol (indicated as OA) were applied to hairless mouse skin (each animal received 100 µg of ENX) and the in vivo ENX delivery efficiencies were compared. Skin deposition profiles of ENX over 96 h are depicted in A) for DMs and B) for OA formulations. Plasma concentrations of ENX over 96 h treatment of topical gel formulations containing C) DMs and D) OA are also obtained. Error bars: Standard deviation (SD)

We have performed two short-term pharmacokinetic (PK) test for in vivo transdermal delivery of ENX micelles compared to ENX+OA formulation: repeated-dosing (FIGS. 4 and 5), and single dosing (FIG. 6) experiments. In a repeated-dosing study, three-repeated dosing were applied (0, 24, 48 hours) with washing of the treated area with gauze soaked in 70% EtOH prior to the 24 and 48 hour dosing. After the last dosing (48 hrs), ENX formulations were not washed but left on the skin until euthanasia for skin and blood collection. The ENX+OA formulation quickly appeared in systemic circulation during first 48 hrs, and showed relatively stable exposure until the end of the study (96 hrs); the ENX-micelle showed a pattern of delay in systemic exposure, with large variation in delivery between 72 and 96 hrs; overall, we found no significant difference in plasma concentration between two gel treatment groups (p=0.7).

These three repeated daily treatments showed that ENX-micelle (DM) and ENX-OA formulation built consistent skin deposits of ENX which could serve as ENX reservoir for prolonged release. This in vivo result does not correlate with our in vitro skin permeation data, which showed that permeation of ENXDM was 2× higher than ENX-OA at 24 hr. A possible reason is that drying of the ENX-micelle formulation during the in-vivo experiment led to aggregation of DM polymers and gelling polymers; thus ENX-micelle may require a prolonged support of the vehicle (water) to exhibit the higher permeation observed in vitro. In our next experiment we will achieve occlusive conditions to prevent evaporation of moisture from the gel formulation.

Figure 6:
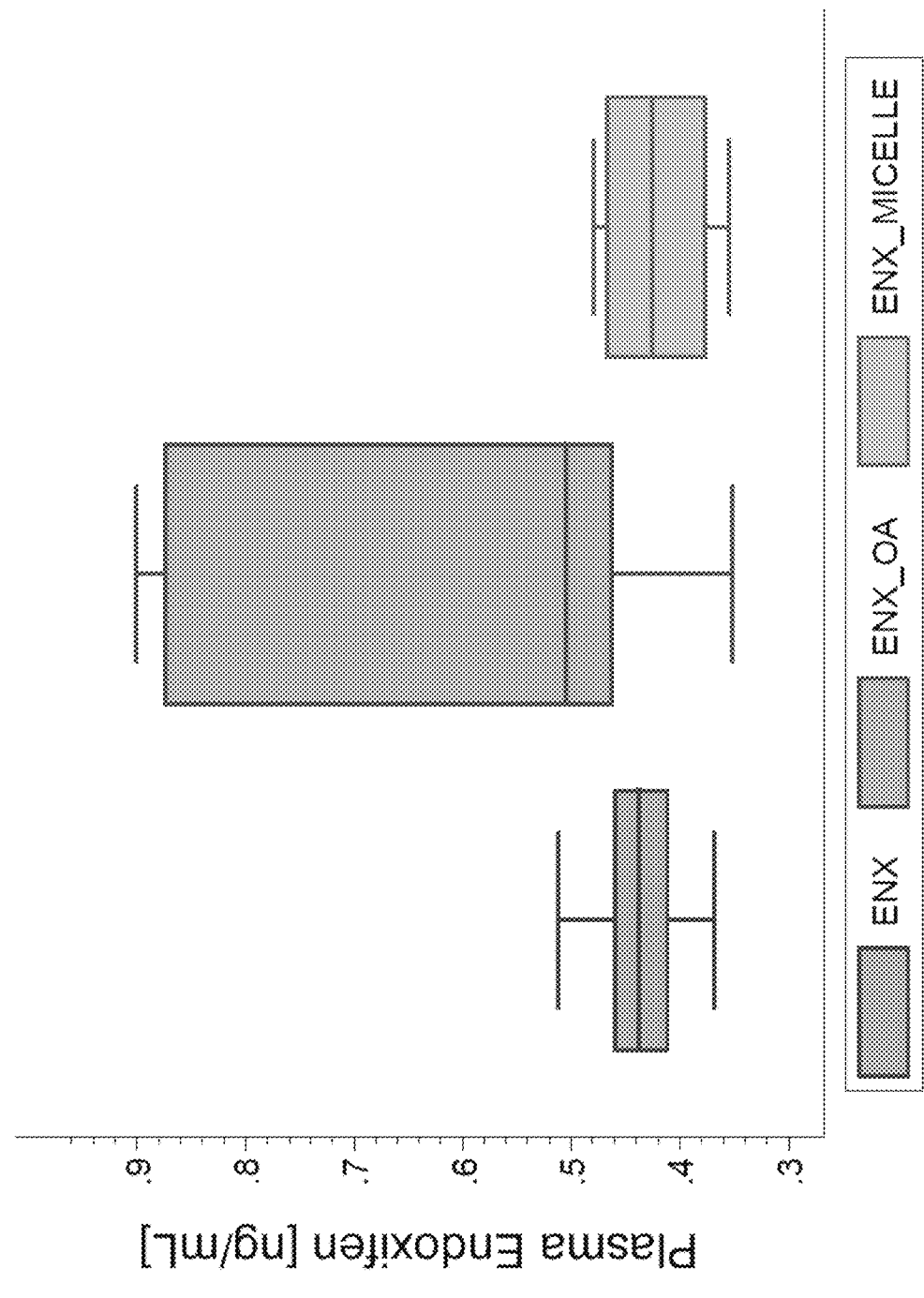
FIG. 6. In vivo plasma concentration of ENX after topical gel treatments under heavy occlusive conditions. ENX-loaded DMs in Klucel gel (indicated as DMs) or free ENX dispersed in Klucel gel containing 0.5% OA and 60% ethanol (indicated as OA) were applied to hairless mouse skin (each animal received 0.1 mg of ENX) and the in vivo ENX delivery efficiencies were compared. Plasma concentrations of ENX at 72 h treatment of topical gel formulations containing: EtOH, ethanol (60%, v/v); DM, dendron micelle; EtOH/OA, ethanol (60% v/v) with OA (0.5%, v/v).

In the second in vivo permeation study (under heavy occlusive conditions), Klucel gel containing 100 µL of ENX either loaded in DMs or dispersed in the OA/ethanol cosolvent system was applied to the hairless mice (FIG. 6). Single dose was applied to the animals, and were maintained for 72 h under heavy occlusive conditions provided by the double layers of Tegaderm®. The skin deposition of ENX after 72 h of treatments was measured using HPLC. Compared to 1.6% obtained from the OA-ethanol group, a lower Permeation % of ENX was obtained from the DM group (0.8%), which is similar to the ethanol group.

Example 4—Endoxifen Gel for Local Transdermal Therapy to the Breast

Despite large Phase III clinical trials that have established the success of selective estrogen receptor modulators (SERMs) for breast cancer prevention[1] and therapy of duct carcinoma in situ (DCIS) [2], the acceptance of tamoxifen (TAM) by women at high risk for breast cancer has been low. Reasons include quality of life impairments, the possibility of serious side effects, and reluctance by healthy women to take oral medication for prevention. However, breast cancer prevention requires only that the breast be exposed to the drug; systemic exposure is both unnecessary and harmful. For example, 5 years of systemic exposure with oral TAM leads to benefits to the breast and bone, but with costs to quality of life, and health [2-4]. An alternative to oral delivery is that of transdermal delivery of drugs through the breast skin; its advantages include low systemic exposure, the avoidance of fast hepatic metabolism, and simplicity of application which will allow dissemination across the globe. Therefore, local transdermal therapy (LTT) to the breast is likely to improve the tolerability and the acceptance of pharmacological cancer prevention regimens by women.

The unique features of the breast predict the success of LTT. These include the embryological origin of the breast as a skin appendage (a modified eccrine gland) [5] with a well-developed internal lymphatic circulation [6], and the presence of a subcutaneous and retromammary fatty envelope. Previous studies of LTT, including our recently completed pre-operative trial testing 4-hydroxytamoxifen (4-OHT) gel in women with ductal carcinoma in situ (DCIS), suggest that delivery is local with minimal systemic exposure, and good biological effect [7-9]. The formulation of 4-OHT that we previously used is no longer available, but we have performed preliminary testing of the dermal permeation of endoxifen (ENX, the other major active metabolite of TAM) which suggest that ENX is in fact more suitable than 4-OHT for transdermal delivery [10]. We therefore propose developing a further transdermal formulation of ENX, to enable clinical trials in women at high risk for breast cancer, and those with DCIS.

Endoxifen is particularly well suited for development as a breast LTT agent. Like 4-OHT, the binding affinities of ENX are 25-fold greater for ERα and 56-fold greater for ERβ than that of TAM [11,12]. ENX is expected to be more efficacious than 4-OHT related to its proteosomic degradation of ERα, and the possibility of more selective anti-estrogenic effects [13-15]. Its specific toxicity profile is under study, but results from the Mayo group suggest that, in terms of uterine weight, luminal epithelial cell height, and cell proliferation in the stroma and luminal epithelium of the uterus, ENX has similar uterotrophic effects to TAM when administered orally to rats [16]. If it shares the toxicity of the parent drug and its dermal permeation is equivalent to that of 4-OHT (or better), ENX is an excellent candidate for LTT. Additionally, the chemical structure of ENX would render it more suitable for transdermal delivery. It is smaller and more polar than 4-OHT; one methyl group at a tertiary amine is replaced with a hydrogen, resulting in a secondary amine, which is more hydrophilic than the tertiary amine of 4-OHT. With the addition of a permeation enhancer such as oleic acid (OA) which makes the stratum corneum fluidic [17,18] and ethanol, which gives a continuous driving force [19,20], ENX moves faster through the skin than 4-OHT. The amine group of ENX may provide a favorable balance of hydrophilic and hydrophobic properties, making ENX traverse the stratum corneum more easily.

We propose that Endoxifen, formulated in an alcoholic solution, with a permeation enhancer, will penetrate the breast skin safely, and will be selectively retained in the breast in sufficient quantities for efficacious breast cancer prevention. At the same time, systemic concentrations will be sufficiently low to avoid systemic toxicity. Our objectives include: 1) to develop and produce a transdermal formulation of endoxifen, 2) define optimal dosing, 3) and establish safety of transdermal delivery, leading to a successful IND application for a clinical trial. Support for our proposal comes from prior studies demonstrating that the closely-related molecule, 4-OHT, when applied to the breast skin in an alcohol-based gel, is concentrated in breast parenchyma to a greater degree than when applied to skin elsewhere, with low systemic concentrations [7]. The concentrations achieved in the mammary gland are sufficient to inhibit cell proliferation of invasive cancer [8] and DCIS [9] to a similar extent as the standard oral dose of tamoxifen (20 mg). With the avoidance of first pass hepatic metabolism, coagulation pathways were not activated, and sex hormone binding globulin and insulin-like growth factor 1 remained unchanged, in contrast to the oral tamoxifen group, where all the expected changes were seen [9]. Thus, in a Phase II clinical trial, we demonstrated that 4-OHT applied to the breast skin 1) penetrates the skin, 2) concentrates in the breast, 3) decreases proliferation of DCIS cells, 4) results in low circulating levels, 5) does not activate coagulation pathways or measures of estrogenicity.

The selective concentration in the breast of drugs applied to the breast skin has been further validated in a trial using a non-SERM drug, diclofenac (see Example 1). The mean diclofenac breast tissue concentrations were 6-fold higher in the breast patch than in the abdominal patch group, even in areas that did not underlie the patch; and were particularly high in fatty samples of tissue.

Given the excellent suitability of endoxifen for LTT, we have shown in vitro that an alcoholic solution of ENX (0.2 mg/mL), with 0.5% oleic acid as a permeation enhancer, penetrates human skin efficiently, with lag time, flux, and absorption optimized at this concentration[10]. These permeation parameters compare favorably to those of estradiol, a widely used and well established transdermal agent. We have tested this formulation in an in vivo study, using nude rats (see Example 2), which demonstrated that excellent permeation is achieved, with the highest concentrations of ENX being present in the axillary mammary gland (the site of application of the ENX gel). The mammary gland concentration was 7 fold higher with LTT than with oral TAM therapy, but plasma levels were statistically similar with LTT and oral therapy (see Example 2 for detailed discussion of this finding). Similar results were obtained in short-term pharmacokinetic (PK) studies in mice, where we compared our ENX-OA formulation to an ENX-micelle formulation (see Example 3). The ENX-micelle formulation was superior in vitro [21] but the ENX-OA formulation performed as well or better in an in vivo mouse study.

Our overall research strategy is designed to enable IND approval in preparation for a clinical trial which will mimic our previous pre-surgical window study of 4-OHT gel in women requiring surgery for DCIS [9]. We submit that further rat studies are not required for this purpose. An oral repeated-dose GLP rodent toxicity study of ENX has already been performed by NCI. A report from Jina Pharmaceuticals using ENX citrate shows efficacy against a MCF-7 xenograft model in female nude mice with a dose of 2-8 mg/kg; pharmacokinetic (PK) data show that orally administered ENX results in faster and higher systemic bioavailability than TAM in female SD rats. [22]. Additionally, the Mayo Clinic has initiated phase I and II studies with oral ENX, with MTT not reached at an oral dose of 160 mg daily. Thus the equivalence (and possible superiority) of ENX to TAM appears fairly certain, and for our purposes only dermal toxicology and PK studies of transdermal ENX gel in non-rodent species are required. In this light, our PREVENT application entails 1) producing the topical formulation of ENX for human use, 2) generating preclinical dermal toxicity and pharmacokinetic data in non-rodent species, as required by the FDA for granting of an IND, 3) providing data on optimal dosing, with specific attention to the highest topical dose that is not associated with dermal or uterine toxicity, (and potentially, on activation of coagulation pathways). Our reasoning for the experimental plan proposed to the NCI is rationalized below.

Testing of Dermal Permeation and Intramammary Concentrations of Endoxifen:

Our in vitro (human skin)[10] and in vivo (rodent) data (details in Example 2) demonstrates that ENX in a 60% alcoholic gel, with 0.5% oleic acid, penetrates well and concentrates best in the mammary gland to which it is applied. Briefly, in a non-GLP study, we randomized nude rats into four groups (no treatment, oral TAM (3 mg/kg/day), 4-OHT gel (1 mg/kg/day), ENX gel (1 mg/kg/day), and treated them daily. There were no deaths, no weight loss, and no skin irritation at the end of the experiment. Our goal now is to determine a safe dose that will prevent breast cancer and treat DCIS. This entails defining the minimal effective dose, although we note recent data suggesting that in pre-treated cancer patients efficacy of ENX may be enhanced by higher drug concentrations [23]. However, endometrial proliferation is also increased with higher ENX concentrations [16]. With LTT our focus is on high mammary and low systemic exposure, but there have been few studies of mammary drug concentrations. Gjerde et. al. have reported concentrations of 4-OHT following administration of oral TAM, 1, 5, 20 mg daily for 28 days, showing that ENX concentrations increased in serum (3, 9, and 38 ng/mL, respectively) and in tumor tissue (31, 80, 340 ng/g, respectively)[24]. Endoxifen data were not presented for normal breast tissue, but it is safe to assume that these too will rise with increasing oral (and transdermal) dose.

Data from our previous studies show that women taking oral TAM 20 mg/day for at least 6 weeks, achieved median ENX concentrations in mammary fat of 8 ng/g; in rats receiving oral TAM, the mammary concentration of ENX was ~5 ng/g. In contrast, rats receiving ENX gel (1 mg/kg/day) achieved mammary gland concentrations of 37 ng/g of tissue. Plasma ENX was 6 ng/mL (16 nM) in women treated with oral TAM, 3 ng/mL (8 nM) in oral TAM-treated rats, but 1.8 ng/mL (5 nM) in ENX-gel treated rats. Thus ENX gel, 1 mg/kg/day applied to the rat mammary gland produced a lower plasma concentration than oral TAM in women (5 vs. 16 nM), but a much higher mammary tissue concentration (37 vs 8 ng/g). PK-PD modeling by Gong et. al. shows tumor growth inhibition (TGI) in dose-ranging experiments of oral ENX in MCF7 xenograft bearing mice. The KC50 of plasma ENX was at 14 nM, and optimal TGI at stasis (Cstasis showing 100% TGI) at 53 nM. The simulation using human PK indicates that a 20 mg/day dose of oral TAM results in 63% TGI at day 21, equivalent to 0.5 mg/day oral ENX (67% TGI), while 1 mg and 4 mg/day doses of oral ENX cause 87 and 97% TGI at day 21 in human, respectively [25]. Thus preclinical pharmacology and efficacy data suggest that our rat dose of ENX 1 mg/kg/day is in the efficacious range, and given the expected high mammary concentrations, could potentially be lowered to reach the minimal effective dose.

For the purposes of ENX-LTT, we propose further testing in non-rodent species (guinea pigs for dermal hypersensitivity test, and mini-pig for PK profiling and dermal toxicology, skin-irritation, uterine toxicity. Based on the data above, three doses are proposed: 0.5, 1, and 2 mg/kg/day. Rat dose (1 mg/kg/day of ENX gel) can be converted to 9.7 mg/day (0.16 mg/kg/day) in human, 0.18 mg/kg/day in mini pigs, and 0.74 mg/kg/day in guinea pigs. Therefore, three human equivalent doses (HED)(approximately 5, 10, and 20 mg/day) need to be tested for 90 days in guinea pigs and mini pigs to identify the maximum recommended starting safe dose in DCIS patients.

Dermal Delayed Hypersensitivity Test in Guinea Pigs:

This is required per the FDA Guidance (Nonclinical Safety Evaluation of Reformulated Drug Products and Products Intended for Administration by an Alternate Route).

Repeat Dose PK, Toxicity, Dermal Irritation Study in Female Mini-Pigs:

We expect that ENX gel dose in the range of HED 5-20 mg/day applied to the skin of the mammary glands of mini-pigs, will lead to mammary tissue levels of 10-30 ng/g tissue (at least as high as the 8 ng/g that we observed in women on oral TAM). Although the use of pigs will add to the expense of testing, this is the best non-primate model for skin permeation experiments [25], and there are data showing that the mammary gland and uterine response to estrogens and anti-estrogens parallels the human [26]. The use of mini-pigs will allow measurement of mammary concentrations of ENX (loss of gel through grooming is not an issue for the pig), and uterine response. The mini-pig model has been used successfully by Repros Therapeutics in developing data for IND submission for telapristone gel for breast LTT (the study is approved for funding by DCP and is expected to open shortly).

Clinical Trial of ENX-LTT for DCIS Patients:

Once data required for dosing and FDA/IND status is acquired, we anticipate a clinical trial similar to our 4-OHT gel study, in women undergoing surgery for hormone receptor positive DCIS with decrease in Ki67 labeling as the primary endpoint. The design would be a Phase IIB randomized trial of ENX gel versus oral TAM in women with core-biopsy proven, newly diagnosed DCIS who require surgical therapy. The primary assay for efficacy would be Ki67 LI of the DCIS. Supporting secondary assays would include measures of toxicity [9], as well as drug concentration in serum and tissue. The ENX LTT gel dose will be selected from the pig studies, using the dose that is closest to mammary concentrations seen in pigs receiving oral TAM, but not producing uterine changes. However, doses selected for LTT are considerably lower than those being tested for systemic therapy of advanced disease, and we do not expect to see significant toxicity at these doses. For the clinical trial, oral endoxifen could be considered as the control arm (rather than TAM); this will produce novel data and a more direct comparison between oral therapy and LTT. It will require that optimal oral dosing data on ENX are available at the time the trial is designed.

REFERENCES

1. Cuzick J, Sestak I, Bonanni B, Costantino J P, Cummings S, Decensi A et al.: Selective oestrogen receptor modulators in prevention of breast cancer: an updated meta-analysis of individual participant data. *Lancet* 2013, 381: 1827-1834.
2. Fisher B, Costantino J P, Wickerham D L, Redmond C K, Kavanah M, Cronin W M et al.: Tamoxifen for prevention of breast cancer: Report of the National Surgical Adjuvant Breast and Bowel Project P-1 Study. *J Natl Cancer Inst* 1998, 90: 1371-1388.
3. Port E R, Montgomery L L, Heerdt A S, Borgen P I: Patient reluctance toward tamoxifen use for breast cancer primary prevention. *Ann Surg Oncol* 2001, 8: 580-585.
4. Day R, Ganz P A, Costantino J P, Cronin W M, Wickerham D L, Fisher B: Health-related quality of life and tamoxifen in breast cancer prevention: a report from the National Surgical Adjuvant Breast and Bowel Project P-1 Study. *J Clin Oncol* 1999, 17: 2659-2669.
5. Ackerman A B, Kessler G, Gyorfi T, Tsou H C, Gottlieb G J: Contrary view: the breast is not an organ per se, but a distinctive region of skin and subcutaneous tissue. *Am J Dermatopathol* 2007, 29: 211-218.
6. Suami H, Pan W R, Mann G B, Taylor G I: The lymphatic anatomy of the breast and its implications for sentinel lymph node biopsy: a human cadaver study. *Ann Surg Oncol* 2008, 15: 863-871.
7. Pujol H, Girault J, Rouanet P, Fournier S, Grenier J, Simony J et al.: Phase I study of percutaneous 4-hydroxy-tamoxifen with analyses of 4-hydroxy-tamoxifen concentrations in breast cancer and normal breast tissue. *Cancer Chemother Pharmacol* 1995, 36: 493-498.
8. Rouanet P, Linares-Cruz G, Dravet F, Poujol S, Gourgou S, Simony-Lafontaine J et al.: Neoadjuvant percutaneous 4-hydroxytamoxifen decreases breast tumoral cell proliferation: a prospective controlled randomized study comparing three doses of 4-hydroxytamoxifen gel to oral tamoxifen. *J Clin Oncol* 2005, 23: 2980-2987.
9. Lee O, Page K, Ivancic D, Helenowski I, Parini V, Sullivan M E et al.: A Randomized Phase II Presurgical Trial of Transdermal 4-Hydroxytamoxifen Gel versus Oral Tamoxifen in Women with Ductal Carcinoma In Situ of the Breast. *Clin Cancer Res* 2014, 20: 3672-3682.

10. Lee O, Ivancic D, Chatterton R T, Rademaker A, Khan S A: In vitro human skin permeation of endoxifen: potential for local transdermal therapy for primary prevention and carcinoma in situ of the breast. *Breast Cancer: Targets and Therapy* 2011, 3: 61-70.
11. Lim Y C, Desta Z, Flockhart D A, Skaar T C: Endoxifen (4-hydroxy-N-desmethyl-tamoxifen) has antiestrogenic effects in breast cancer cells with potency similar to 4-hydroxy-tamoxifen. *Cancer Chemother Pharmacol* 2005, 55: 471-478.
12. Lim Y C, Li L, Desta Z, Zhao Q, Rae J M, Flockhart D A et al.: Endoxifen, a secondary metabolite of tamoxifen, and 4-OH-tamoxifen induce similar changes in global gene expression patterns in MCF-7 breast cancer cells. *J Pharmacol Exp Ther* 2006, 318: 503-512.
13. Goetz M P, Rae J M, Suman V J, Safgren S L, Ames M M, Visscher D W et al.: Pharmacogenetics of tamoxifen biotransformation is associated with clinical outcomes of efficacy and hot flashes. *J Clin Oncol* 2005, 23: 9312-9318.
14. Goetz M P, Knox S K, Suman V J, Rae J M, Safgren S L, Ames M M et al.: The impact of cytochrome P450 2D6 metabolism in women receiving adjuvant tamoxifen. *Breast Cancer Res Treat* 2007, 101: 113-121.
15. Wu X, Hawse J R, Subramaniam M, Goetz M P, Ingle J N, Spelsberg T C: The tamoxifen metabolite, endoxifen, is a potent antiestrogen that targets estrogen receptor alpha for degradation in breast cancer cells. *Cancer Res* 2009, 69: 1722-1727.
16. Schweikart K M, Eldridge S R, Safgren S L, Parman T, Reid J M, Ames M M et al.: Comparative Uterotrophic Effects of Endoxifen and Tamoxifen in Ovariectomized Sprague-Dawley Rats. *Toxicol Pathol* 2014.
17. Fang J Y, Hwang T L, Leu Y L: Effect of enhancers and retarders on percutaneous absorption of flurbiprofen from hydrogels. *Int J Pharm* 2003, 250: 313-325.
18. Yu B, Dong C Y, So P T, Blankschtein D, Langer R: In vitro visualization and quantification of oleic acid induced changes in transdermal transport using two-photon fluorescence microscopy. *J Invest Dermatol* 2001, 117: 16-25.
19. Ogiso T, Paku T, Iwaki M, Tanino T: Percutaneous penetration of fluorescein isothiocyanate-dextrans and the mechanism for enhancement effect of enhancers on the intercellular penetration. *Biol Pharm Bull* 1995, 18: 1566-1571.
20. Williams A C, Barry B W: Penetration enhancers. *Adv Drug Deliv Rev* 2004, 56: 603-618.
21. Y. Yang, R. Pearson, O. Lee, R. C. Chatterton, S. A. Khan, S. Hong (Eds): Dendron-based micelles for topical delivery of endoxifen: A potential chemo-preventive medicine for breast cancer. In *Advanced Functional Materials* 2014, 24: 2442-2449.
22. Ahmad A, Ali S M, Ahmad M U, Sheikh S, Ahmad I: Orally administered endoxifen is a new therapeutic agent for breast cancer. *Breast Cancer Res Treat* 2010, 122: 579-584.
23. Hawse J R, Subramaniam M, Cicek M, Wu X, Gingery A, Grygo S B et al.: Endoxifen's molecular mechanisms of action are concentration dependent and different than that of other anti-estrogens. *PLoS One* 2013, 8: e54613.
24. Gjerde J, Gandini S, Guerrieri-Gonzaga A, Haugan Moi L L, Aristarco V, Mellgren G et al.: Tissue distribution of 4-hydroxy-N-desmethyltamoxifen and tamoxifen-N-oxide. *Breast Cancer Res Treat* 2012, 134: 693-700.
25. Gong I Y, Teft W A, Ly J, Chen Y H, Alicke B, Kim R B et al.: Determination of clinically therapeutic endoxifen concentrations based on efficacy from human MCF7 breast cancer xenografts. *Breast Cancer Res Treat* 2013, 139: 61-69.
26. Goodrich J A, Clarkson T B, Cline J M, Jenkins A J, Del Signore M J: Value of the micropig model of menopause in the assessment of benefits and risks of postmenopausal therapies for cardiovascular and reproductive tissues. *Fertil Steril* 2003, 79 Suppl 1: 779-788\

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating breast cancer and ductal cancer in situ (DCIS) in a patient in need thereof, the method comprising administering topically to the breast or breasts of the patient a topical formulation comprising an effective dose of endoxifen for treating breast cancer, wherein after administering the topical formulation topically to the breast or breasts of the patient, an effective concentration of endoxifen for treating breast cancer and ductal cancer in situ (DCIS) is delivered to the breast or breasts of the patient.

2. The method of claim 1, wherein the topical formulation is a transdermal formulation comprising one or more chemical permeation enhancers (CPEs).

3. The method of claim 1, wherein the topical formulation comprises a fatty acid at a concentration of about 0.1%-5% (w/w), the fatty acid having a melting temperature of less than about 20° C.

4. The method of claim 3, wherein the fatty acid is oleic acid.

5. The method of claim 1, wherein the topical formulation comprises alcohol at a concentration of about 40%-80% (w/w).

6. The method of claim 1, wherein the topical formulation is a gel comprising a gelling polymer at a concentration of about 0.1%-0.5% (w/w).

7. The method of claim 1, wherein the endoxifen is present in the topical formulation at a concentration of about 0.1 mg/ml 10 mg/ml.

8. The method of claim 1, wherein the endoxifen is administered at a dose per bodyweight of the patient of about 1.0-20 mg/kg/day.

9. The method of claim 1, wherein the dose of endoxifen delivered to the breast of the patient is at least about 1.0-20 ng/g and the dose delivered to the plasma of the patient is no more than about 5 ng/ml.

10. The method of claim 1, wherein the ratio (R) of the dose of endoxifen delivered to the breast of the patient ($D_{Breast}$ in ng/g) to the dose delivered to the plasma of the patient ($D_{Plasma}$ in ng/ml) is greater than about 5.

11. A topical formulation for treating breast cancer and ductal cancer in situ (DCIS) in a patient in need thereof, the topical formulation comprising an effective dose of endoxifen for treating breast cancer, wherein after the topical formulation is administered topically to the breast or breasts of the patient, an effective concentration of endoxifen for treating breast cancer and ductal cancer in situ (DCIS) is delivered to the breast or breasts of the patient.

12. The topical formulation of claim 11, wherein the topical formulation is a transdermal formulation comprising one or more chemical permeation enhancers (CPEs).

13. The topical formulation of claim 11, wherein the topical formulation comprises a fatty acid at a concentration of about 0.1%-5% (w/w), the fatty acid having a melting temperature of less than about 20° C.

14. The topical formulation of claim 13, wherein the fatty acid is oleic acid.

15. The topical formulation of claim 11, wherein the topical formulation comprises alcohol at a concentration of about 10%-80% (w/w).

16. The topical formulation of claim 11, wherein the topical formulation is a gel comprising a gelling polymer at a concentration of about 0.1%-0.5% (w/w).

17. The topical formulation of claim 11, wherein the endoxifen is present in the topical formulation at a concentration of about 0.1 mg/ml 10 mg/ml.

18. The topical formulation of claim 11, wherein the topical formulation is formulated to deliver a dose of endoxifen per bodyweight of the patient of about 1.0-20 mg/kg/day.

19. The topical formulation of claim 11, wherein the dose of endoxifen delivered to the breast of the patient is at least about 1.0-20 ng/g and the dose delivered to the plasma of the patient is no more than about 5 ng/ml.

20. The topical formulation of claim 11, wherein the topical formulation is formulated to deliver a dose of endoxifen to the breast of the patient ($D_{Breast}$) and a dose of endoxifen to the plasma of the patient ($D_{Plasma}$) and the ratio (R) of the dose of endoxifen delivered to the breast of the patient ($D_{Breast}$ in ng/g) to the dose delivered to the plasma of the patient ($D_{Plasma}$ in ng/ml) is greater than about 5.

* * * * *